(12) United States Patent
Suddaby

(10) Patent No.: US 12,048,466 B2
(45) Date of Patent: *Jul. 30, 2024

(54) FUSION DEVICE

(71) Applicant: Loubert S. Suddaby, Orchard Park, NY (US)

(72) Inventor: Loubert S. Suddaby, Orchard Park, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 18/156,452

(22) Filed: Jan. 19, 2023

(65) Prior Publication Data

US 2023/0157739 A1 May 25, 2023

Related U.S. Application Data

(63) Continuation of application No. 17/062,102, filed on Oct. 2, 2020, now Pat. No. 11,583,326, which is a
(Continued)

(51) Int. Cl.
*A61B 17/86* (2006.01)
*A61F 2/30* (2006.01)

(52) U.S. Cl.
CPC ............ *A61B 17/8625* (2013.01); *A61F 2/30* (2013.01); *A61F 2002/3055* (2013.01);
(Continued)

(58) Field of Classification Search
CPC ... A61B 17/86; A61B 17/8625; A61B 17/863; A61B 17/8635; A61B 17/864; A61B 17/8645; A61B 17/8665; A61B 2017/8655
See application file for complete search history.

(56) References Cited

U.S. PATENT DOCUMENTS 4,175,555 A 11/1979 Herbert
5,098,435 A * 3/1992 Stednitz ............ A61B 17/1637
606/907
(Continued)

FOREIGN PATENT DOCUMENTS

| CA | 2390912 | 1/2008 |
| EP | 3123970 | 2/2017 |
| FR | 2971138 | 8/2012 |

OTHER PUBLICATIONS

Rialto SI Fusion System Brochure, "A Unique Approach to Sacroiliac Joint Fusion Procedures", Medtronic, 2016.
(Continued)

*Primary Examiner* — Eric S Gibson
(74) *Attorney, Agent, or Firm* — Harter Secrest & Emery LLP; Michael Nicholas Vranjes

(57) ABSTRACT

A fusion device assembly for fusion of a joint, including a first screw portion, including a first distal end, a first proximal end, a first radially outward facing surface including a first diameter, and a first hole, a second screw portion, including a second distal end, a second proximal end, a second radially outward facing surface including a second diameter, and a second hole, and a section, including a first end connected to the first proximal end, a second end connected to the second distal end, a third radially outward facing surface including a third diameter, the third diameter being less than the first diameter and the second diameter, and a third hole, wherein the first hole, the second hole, and the third hole are in fluid communication.

20 Claims, 23 Drawing Sheets

Related U.S. Application Data continuation-in-part of application No. 16/774,079, filed on Jan. 28, 2020, now Pat. No. 11,172,969.

(52) U.S. Cl.
CPC .............. *A61F 2002/30622* (2013.01); *A61F 2002/30845* (2013.01); *A61F 2002/30851* (2013.01); *A61F 2002/30995* (2013.01)

(56) References Cited

U.S. PATENT DOCUMENTS

| | | | | |
|---|---|---|---|---|
| 5,478,342 | A * | 12/1995 | Kohrs | A61B 17/8685 606/310 |
| 5,759,184 | A * | 6/1998 | Santangelo | A61B 17/742 606/313 |
| 5,849,004 | A * | 12/1998 | Bramlet | A61B 17/0401 606/310 |
| 6,030,162 | A | 2/2000 | Huebner | |
| 6,183,474 | B1 * | 2/2001 | Bramlet | A61B 17/1659 606/65 |
| 7,708,738 | B2 * | 5/2010 | Fourcault | A61B 17/863 606/67 |
| 7,780,710 | B2 * | 8/2010 | Orbay | A61B 17/8061 606/310 |
| 8,475,505 | B2 | 7/2013 | Nebosky et al. | |
| 8,579,947 | B2 | 11/2013 | Wu | |
| 8,617,226 | B2 * | 12/2013 | Kim | A61B 17/864 606/310 |
| 8,945,193 | B2 * | 2/2015 | Kirschman | A61B 17/8841 606/317 |
| 8,992,587 | B2 * | 3/2015 | Kirschman | A61B 17/7064 606/305 |
| 9,295,488 | B2 | 3/2016 | Asfora | |
| 9,308,035 | B2 * | 4/2016 | Biedermann | A61B 17/744 |
| 9,358,056 | B2 | 6/2016 | Stalcup et al. | |
| 9,358,057 | B1 | 6/2016 | Whipple et al. | |
| 9,480,520 | B2 | 11/2016 | Rampersaud et al. | |
| 9,526,547 | B2 * | 12/2016 | Reed | A61B 17/864 |
| 9,668,781 | B2 | 6/2017 | Stark | |
| 9,833,321 | B2 | 12/2017 | Rindal et al. | |
| 9,931,141 | B2 | 4/2018 | Jimenez | |
| 10,172,656 | B1 * | 1/2019 | Reimels | A61B 17/8625 |
| 10,251,688 | B2 | 4/2019 | Asfora | |
| 10,499,969 | B2 * | 12/2019 | McGirt | A61B 17/7032 |
| 10,864,029 | B2 * | 12/2020 | Redmond | A61B 17/8685 |
| 11,172,969 | B2 * | 11/2021 | Suddaby | A61B 17/844 |
| 11,583,326 | B2 * | 2/2023 | Suddaby | A61B 17/8625 |
| 2002/0049447 | A1 * | 4/2002 | Li | A61B 17/68 606/313 |
| 2002/0143401 | A1 * | 10/2002 | Michelson | A61F 2/446 606/264 |
| 2002/0169453 | A1 * | 11/2002 | Berger | A61B 17/60 606/295 |
| 2003/0014054 | A1 | 1/2003 | Huebner | |
| 2003/0078584 | A1 | 4/2003 | Tipirneni | |
| 2003/0158557 | A1 * | 8/2003 | Cragg | A61B 17/1757 606/86 R |
| 2005/0177158 | A1 * | 8/2005 | Doubler | A61B 17/7225 606/66 |
| 2007/0233123 | A1 * | 10/2007 | Ahmad | A61B 17/864 606/307 |
| 2008/0009861 | A1 * | 1/2008 | Stark | A61B 17/68 606/914 |
| 2010/0057141 | A1 * | 3/2010 | Abdelgany | A61B 17/8685 606/301 |
| 2011/0213426 | A1 * | 9/2011 | Yedlicka | A61B 17/864 606/309 |
| 2013/0018427 | A1 | 1/2013 | Pham et al. | |
| 2013/0123857 | A1 * | 5/2013 | Biedermann | A61B 17/84 606/303 |
| 2013/0310883 | A1 * | 11/2013 | Levy | A61B 17/863 606/313 |
| 2013/0317503 | A1 | 11/2013 | Songer et al. | |
| 2014/0058460 | A1 * | 2/2014 | Reed | A61B 17/863 606/301 |
| 2014/0094859 | A1 * | 4/2014 | Reed | A61B 17/863 606/315 |
| 2014/0121707 | A1 | 5/2014 | Stark | |
| 2014/0243912 | A1 * | 8/2014 | Mobasser | A61B 17/8635 606/311 |
| 2014/0257412 | A1 | 9/2014 | Patty et al. | |
| 2014/0277186 | A1 | 9/2014 | Granberry et al. | |
| 2015/0201979 | A1 * | 7/2015 | Paul | A61B 17/7233 606/62 |
| 2016/0242820 | A1 * | 8/2016 | Whipple | A61B 17/8685 |
| 2016/0287301 | A1 * | 10/2016 | Mehl | A61B 17/8685 |
| 2017/0196608 | A1 * | 7/2017 | Castaneda | A61B 17/84 |
| 2017/0296245 | A1 * | 10/2017 | Gault | A61B 17/8875 |
| 2017/0296344 | A1 | 10/2017 | Souza et al. | |
| 2018/0055551 | A1 * | 3/2018 | Yalizis | A61B 17/68 |
| 2018/0116814 | A1 | 5/2018 | Sullivan et al. | |
| 2018/0153698 | A1 | 6/2018 | Rindal et al. | |
| 2018/0235670 | A1 | 8/2018 | Jimenez | |
| 2019/0125371 | A1 * | 5/2019 | Asfora | A61B 17/1615 |
| 2019/0125408 | A1 * | 5/2019 | Asfora | A61B 17/8625 |
| 2019/0231405 | A1 * | 8/2019 | Redmond | A61B 17/7055 |
| 2019/0231406 | A1 | 8/2019 | Asfora | |
| 2019/0388131 | A1 * | 12/2019 | Mehl | A61B 17/1635 |
| 2020/0038070 | A1 * | 2/2020 | Suddaby | A61F 2/4405 |
| 2020/0046413 | A1 * | 2/2020 | Thornes | A61B 17/863 |
| 2021/0228250 | A1 * | 7/2021 | Suddaby | A61B 17/869 |
| 2021/0228363 | A1 * | 7/2021 | Suddaby | A61F 2/30988 |
| 2023/0157739 | A1 * | 5/2023 | Suddaby | A61F 2/30988 623/18.11 |

OTHER PUBLICATIONS

Sicure® Sacroiliac Joint Fusion System Brochure, Alevio, LLC, Birmingham, AL, 2019.
www.spinemarketgroup@gmail.com, last accessed Apr. 15, 2020.
Acutrak 2® Headless Compression Screw System, Surgical Technique Guide Brochure, 2012 Acumed®, Hillsboro, OR, www.acumed.net, last accessed Apr. 15, 2020.

* cited by examiner

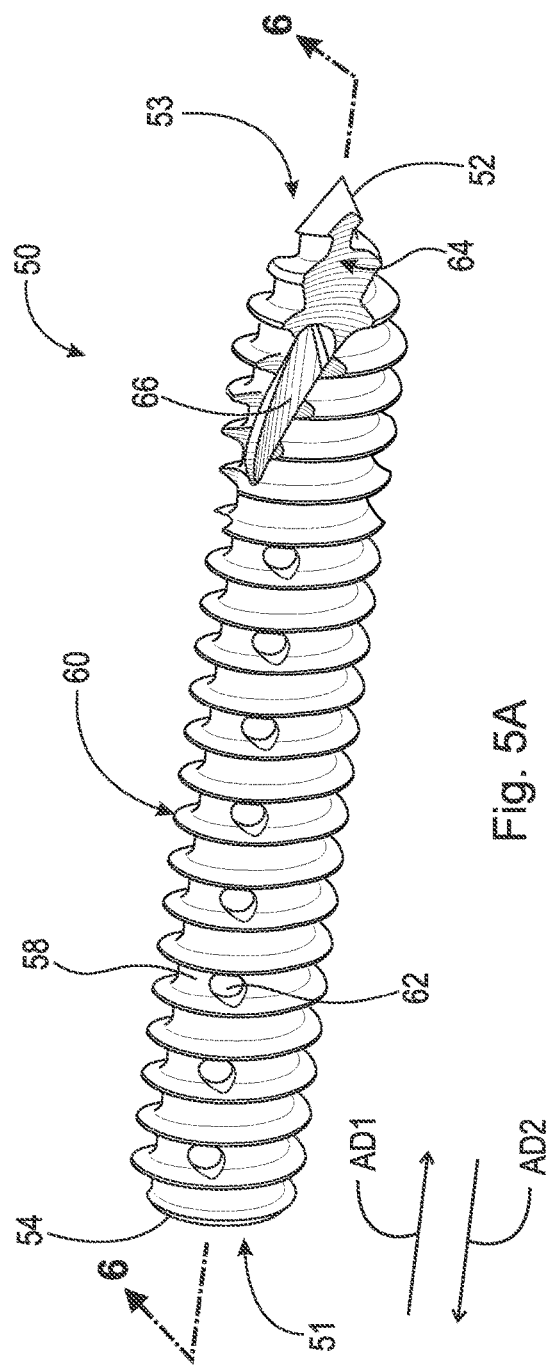
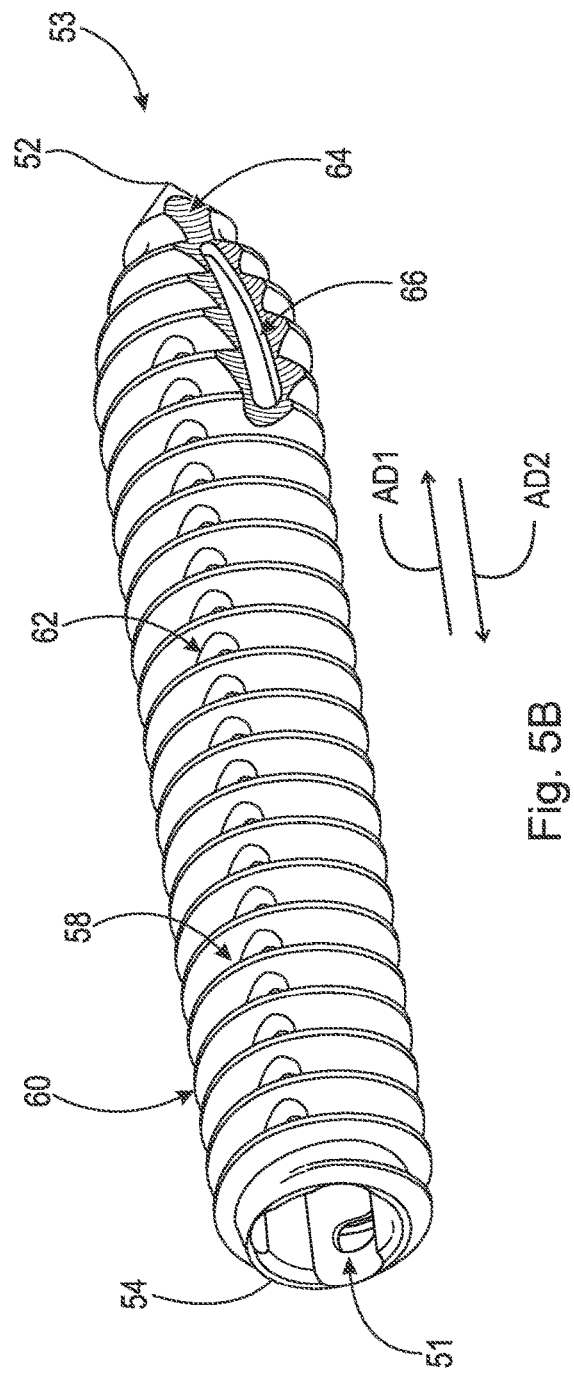
Fig. 5A
Fig. 5B

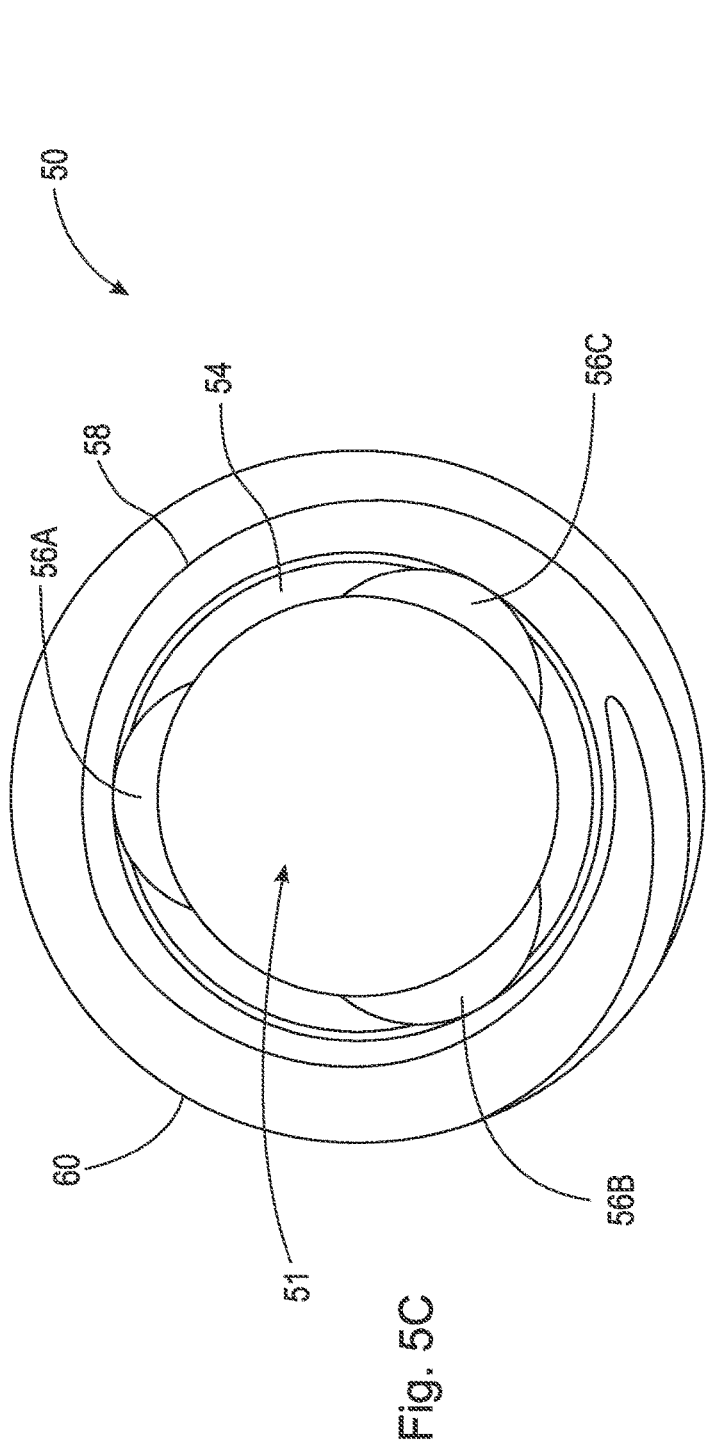
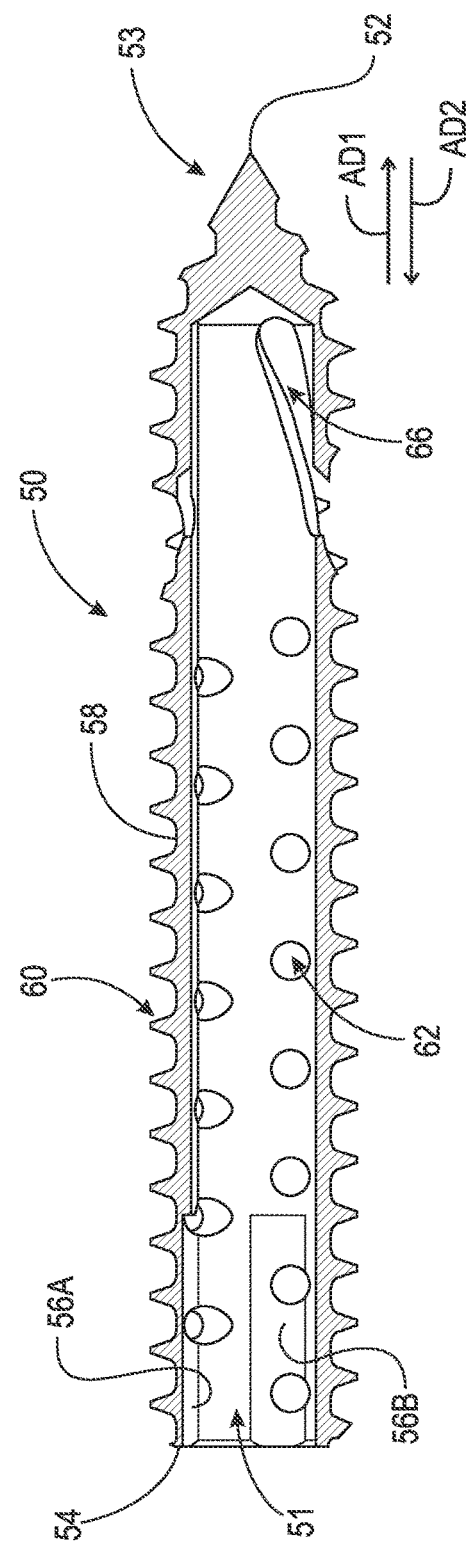
Fig. 5C
Fig. 6

FUSION DEVICE

CROSS-REFERENCE TO RELATED APPLICATIONS

This application is filed under 35 U.S.C. § 120 as a continuation of U.S. patent application Ser. No. 17/062,102, filed on Oct. 2, 2020, which application is a continuation-in-part of U.S. patent application Ser. No. 16/774,079, filed on Jan. 28, 2020, which issued as U.S. Pat. No. 11,172,969 on Nov. 16, 2021, which applications are hereby incorporated by reference in their entireties.

FIELD

The present disclosure relates to orthopedic surgery, and more particularly to interbone fixation fusion devices and especially interarticular joint fixation, specifically deep tissue joints such as spinal facet joints and sacroiliac (SI) joints.

BACKGROUND

Fusion of spinal elements has been a long-standing solution to symptoms of degenerating spinal discs. In fact, even though artificial discs have made some progress in the surgical arena, spinal fusion remains the most reliable means of alleviating symptoms referable to degenerating discs and is still the de facto gold standard.

One of the consequences of spinal fusion is adjacent level degeneration. Even though a normal functional spinal segment is fused, spinal motion must still occur, with forces being transferred to adjacent normal segments placing them under increases stress and contributing to a more rapid degenerative decline.

Since most spinal fusions are done in the low back and include the sacrum, which fuses naturally after birth, caudally transferred forces are dispersed to the sacroiliac (SI) joints causing abnormal stresses upon these joints.

While cranially transmitted forces simply go to the disc above, which can be fused by traditional means of interbody and/or posterolateral fusion, the SI joint is unique, complex, and difficult to visualize with traditional fluoroscopic methods.

Successful spinal fusions are often plagued after months or years of successful relief of symptomatology by a return of symptoms due to adjacent level degeneration. As many as twenty-five percent (25%) of cases of recurrent pain post spinal fusion are felt to be secondary to increased and abnormal motion at the level of the SI joint which can be severe.

While SI joint fusion procedures have been around for many years, recent trends have focused on minimally invasive ways to stabilize the joint thereby alleviating pain caused by the abnormal stresses placed upon them through natural degeneration or accelerated degeneration caused by spinal fusion. The addition of computerized guidance systems to the operating room armamentarium has afforded additional ways that stabilization of complex and deep-seated joints can be achieved surgically.

Thus, there is a long-felt need for a fusion device that allows fusion of deep-seated joints by way of minimally invasive surgery.

SUMMARY

According to aspects illustrated herein, there is provided a fusion device assembly for fusion of a joint, comprising a first screw portion, including a first distal end, a first proximal end, a first radially outward facing surface comprising a first diameter, and a first hole, a second screw portion, including a second distal end, a second proximal end, a second radially outward facing surface comprising a second diameter, and a second hole, and a section, including a first end connected to the first proximal end, a second end connected to the second distal end, a third radially outward facing surface comprising a third diameter, the third diameter being less than the first diameter and the second diameter, and a third hole, wherein the first hole, the second hole, and the third hole are in fluid communication.

In some embodiments, the first screw portion further comprises threading arranged on the first radially outward facing surface, at least one flute extending from the first distal end to the first proximal end, and at least one cutting edge operatively arranged to cut through bone. In some embodiments, the second screw portion further comprises threading arranged on the second radially outward facing surface. In some embodiments, the threading on the first radially outward facing surface includes a first pitch and the threading on the second radially outward facing surface includes a second pitch, the second pitch being different than the first pitch. In some embodiments, the first pitch is greater than the second pitch. In some embodiments, the first pitch is less than the second pitch.

In some embodiments, the first screw portion comprises a first flute including a first cutting edge, the first cutting edge arranged proximate the first distal end and arranged to cut when the first screw portion is displaced in a first circumferential direction, and a second flute including a second cutting edge, the second cutting edge arranged proximate the first proximal end and arranged to cut when the first screw portion is displaced in a second circumferential direction, opposite the first circumferential direction. In some embodiments, the second screw portion further comprises a head non-rotatably connected to the second proximal end.

In some embodiments, the second hole is a through-hole extending from the second proximal end to the second distal end, and the third hole is a through-hole extending from the first end to the second end. In some embodiments, the first distal end comprises at least one cutting surface operatively arranged to cut through cortical bone. In some embodiments, the first distal end comprises a tapered diameter portion. In some embodiments, the fusion device further comprises an aperture extending radially through at least one of the first screw portion, the second screw portion, and the section. In some embodiments, the section does not comprise threading.

According to aspects illustrated herein, there is provided a fusion device assembly for fusion of a joint, comprising a first screw portion, including a first distal end, a first proximal end, a first radially outward facing surface comprising first threading and a first diameter, and a first hole, a second screw portion, including a second distal end, a second proximal end, a second radially outward facing surface comprising second threading and a second diameter, and a second hole, and a section, including a first end connected to the first proximal end, a second end connected to the second distal end, a third radially outward facing surface comprising a third diameter, the third diameter being less than the first diameter and the second diameter, and a third hole, wherein the first hole, the second hole, and the third hole are in fluid communication.

In some embodiments, the first screw portion further comprises at least one flute extending from the first distal end to the first proximal end, and at least one cutting edge operatively arranged to cut through bone. In some embodiments, the first threading includes a first pitch and the second threading includes a second pitch, the second pitch being different than the first pitch. In some embodiments, the first pitch is greater than the second pitch. In some embodiments, the first pitch is less than the second pitch. In some embodiments, the first screw portion comprises a first flute including a first cutting edge, the first cutting edge arranged proximate the first distal end and arranged to cut when the first screw portion is displaced in a first circumferential direction, and a second flute including a second cutting edge, the second cutting edge arranged proximate the first proximal end and arranged to cut when the first screw portion is displaced in a second circumferential direction, opposite the first circumferential direction. In some embodiments, the second hole is a through-hole extending from the second proximal end to the second distal end, and the third hole is a through-hole extending from the first end to the second end.

According to aspects illustrated herein, there is provided a fusion device assembly for fusion of a joint, comprising a fusion device, including a distal end, a proximal end, a radially outward facing surface including threading, a bore extending from the proximal end, at least one flute arranged proximate the distal end, and at least one aperture arranged adjacent to the at least one flute.

In some embodiments, the threading comprises varying pitch. In some embodiments, the fusion device further comprises a plurality of fusion apertures extending from the radially outward facing surface to the bore. In some embodiments, the proximal end further comprises a coupler. In some embodiments, the coupler comprises one or more coupling lobes. In some embodiments, the fusion device further comprises a shaft, the shaft including a first end, a second end operatively arranged to be non-rotatably connected to the proximal end, and a through-bore extending from the first end to the second end. In some embodiments, the shaft is removably connected to the fusion device. In some embodiments, the fusion device further comprises at least one expandable member arranged in the bore, the at least one expandable member operatively arranged to extend radially outward through at least one opening in the radially outward facing surface. In some embodiments, the fusion device further comprises a radially inward facing surface and a nut operatively arranged to engage the at least one expandable member, the nut being threadably engaged with the radially inward facing surface.

In some embodiments, the at least one expandable member comprises a first pivot fixedly secured to the radially inward facing surface, a second pivot slidably connected to the radially inward facing surface, and a third pivot, wherein when the first pivot is displaced in a first axial direction relative to the proximal end, the third pivot displaces radially outward from the radially outward facing surface. In some embodiments, when the nut is displaced in a first axial direction relative to the proximal end, the at least one expandable member displaces radially outward from the radially outward facing surface. In some embodiments, the at least one expandable member is flexible. In some embodiments, the distal end is a drill bit.

According to aspects illustrated herein, there is provided a fusion device for fusion of a joint, comprising a distal end, a proximal end, a radially outward facing surface including threading, a bore extending from the proximal end, at least one flute arranged proximate the distal end, at least one aperture arranged adjacent to the at least one flute, at least one opening, and at least one expandable member operatively arranged in the bore to expand radially through the at least one opening.

In some embodiments, the fusion device further comprises a plurality of fusion apertures extending from the radially outward facing surface to the bore. In some embodiments, the proximal end further comprises a coupler operatively arranged to be non-rotatably connected to a hollow shaft. In some embodiments, the fusion device further comprises a nut arranged in the bore, the nut operatively arranged to engage the at least one expandable member. In some embodiments, when the nut is displaced in a first axial direction relative to the proximal end, the at least one expandable member displaces radially outward from the radially outward facing surface. In some embodiments, the at least one expandable member comprises a first pivot fixedly secured to the radially inward facing surface, a second pivot slidably connected to the radially inward facing surface, and a third pivot, wherein when the first pivot is displaced in a first axial direction relative to the proximal end, the third pivot displaces radially outward from the radially outward facing surface.

According to aspects illustrated herein, there is provided a fusion device assembly for fusion of a joint, comprising a fusion device, including a distal end having a drill bit, a proximal end, a radially outward facing surface including threading, a bore extending from the proximal end, at least one flute arranged proximate the distal end, at least one aperture arranged adjacent to the at least one flute, at least one opening, and at least one expandable member operatively arranged in the bore to expand radially through the at least one opening, and a shaft, including a first end, a second end operatively arranged to be non-rotatably connected to the proximal end, and a through-bore extending from the first end to the second end.

According to aspects illustrated herein, there is provided a device for fixating the position of proximate elements of a dysfunctional sacroiliac (SI) joint, though it is recognized that miniaturization of the device would allow its use in smaller joints such as those in the lumbar facets, hands, and foot and ankle.

The device broadly comprises a cylindrical inter body implant including a self-drilling tip having full or partial threading internally and/or externally, and a hollow internal chamber into which bone drilling material from the advancing tip is funneled via flutes directing the material into apertures that perforate the device wall.

In a fully threaded iteration, the screw pitch is varied such that compression occurs gradually across the joint as the screw advances. In a partially threaded version, threads and flutes are found at the distal end, followed by a non-threaded perforated middle segment and then smaller pitched threads at the proximal end to facilitate joint compression in the manner of a lag-screw. In some embodiments, the device includes a fully threaded regular pitch bone screw configuration.

At the distal point or tip of the device, multiple configurations may be employed. In some embodiments, the tip is hollowed such that the device can be advanced along a guide wire, like a Kirschner wire (or K-wire). In some embodiments, the tip is a sharp point that is simply pressed into the bone surface such that it retains its position upon rotation in a manner approximating a Brad point drill bit tip. In some embodiments, the device is employed with image guidance where a previously placed guide wire is not necessary since real time information as to drill depth and direction is constantly available. The guide wire iteration is likely to be used in cases using traditional fluoroscopy, whereas the point tip version is expected to be used where image guided technology is available.

Once the tip is apposed to the bone surface, rotation of the device by hand or motor advances the tip of the device in a fashion similar to a standard self-drilling bone drill. Flutes at the tip direct bone drillings into the hollow chamber of the device, where they are housed as graft rather than directed back to the proximal drill hole as a normal twist drill would do. The flutes with their capture apparatus are located in the distal third, closer to the distal tip such that as much bone as possible that is harvested by the distal tip is directed into the inner graft chamber. More proximally, apertures exist in the shaft wall to allow the internal graft to communicate with the outer bone such that through-and-through fusion may occur. Such apertures may be round, oblong, spiral, rectangular, etc., and exist between threads or render the threads discontinuous as desired.

In some embodiments, the proximal end of the device is connected to a hollow drive shaft in a reversible fashion. The connection between the device and the hollow drive shaft may comprise any suitable connection known in the art. For example, a reverse thread screw connection, a press fit, a clasp or O-ring, or as a socket connection. In some embodiments, an image array may be connected to the hollow drive shaft so that the deployment of the device is fully image guided.

The hollow drive shaft, in turn, at its proximal end, is configured so as to permit engagement with hand or motor-powered attachments available in any standard orthopedic operating room. The shaft allows deployment of the device to its intended inter-bone target whereupon the hand or power drive attachment is removed leaving the device in situ with the hollow drive shaft emanating from the wound.

Additional bone product may be placed in the hollow drive shaft and a plunger or ramrod may be used to compress and compact the added bone graft into the device since evidence demonstrates that compression of bone elements facilitates fusion.

Once the graft is fully packed into the device, the plunger is held in place until the hollow shaft is disengaged and both the plunger and the shaft can be removed.

This process permits a safe and minimally invasive placement of a bone/fusion device. Rapid and accurate device placement lowers risks of infection and tissue trauma while reducing expensive operating room time.

By having the deployable device function as its own drill bit, drill tap, autograft harvester, joint fixator, and joint compressor, a SI joint fusion can be accomplished in a fraction of the time and with greater accuracy and success than heretofore possible.

According to aspects illustrated herein, there is provided a fusion device assembly for fusion of a joint, comprising a first screw portion, including a first distal end, a first proximal end, a first radially outward facing surface, and a first hole, a second screw portion, including a second distal end, a second proximal end, and a second radially outward facing surface, and a section, including a first end slidably engaged with the first hole, a second end non-rotatably secured to the second distal end, and a third radially outward facing surface.

In some embodiments, the first screw portion further comprises threading arranged on the first radially outward facing surface, at least one flute extending from the first distal end to the first proximal end, and at least one cutting edge operatively arranged to cut through bone. In some embodiments, the first screw portion comprises a first flute including a first cutting edge, the first cutting edge arranged proximate the first distal end and arranged to cut when the first screw portion is displaced in a first circumferential direction, and a second flute including a second cutting edge, the second cutting edge arranged proximate the first proximal end and arranged to cut when the first screw portion is displaced in a second circumferential direction, opposite the first circumferential direction. In some embodiments, the second screw portion further comprises threading arranged on the second radially outward facing surface. In some embodiments, the second screw portion further comprises a head non-rotatably connected to the second proximal end.

In some embodiments, the fusion device assembly further comprises a second hole extending through the second screw portion and the section. In some embodiments, the fusion device assembly further comprises a rod operatively arranged to extend through the second hole and engage the first screw portion. In some embodiments, when the rod is displaced in a first circumferential direction, one of the first screw portion and the second screw portion is displaced relative to the other of the first screw portion and the second screw portion. In some embodiments, when the rod is displaced in a first circumferential direction the second screw portion and the section are displaced in a axial direction toward the first screw portion. In some embodiments, the first screw portion comprises a first diameter, the second screw portion comprises a second diameter, and the section comprises a third diameter, wherein the third diameter is less than the first diameter and the second diameter. In some embodiments, the first hole comprises at least one notch, and the third radially outward facing surface comprises at least one protrusion operatively arranged to engage the at least one notch to non-rotatably connect the section with the first screw portion.

According to aspects illustrated herein, there is provided a fusion device assembly for fusion of a bone structure or joint, comprising a first screw portion, including a first distal end, a first proximal end, a first radially outward facing surface, and a first hole, a second screw portion, including a second distal end, a second proximal end, and a second radially outward facing surface, a bone graft section, including a first end slidably engaged with the first hole, a second end non-rotatably secured to the second distal end and a third radially outward facing surface, and a rod extending internally through the second screw portion, the bone graft section, and the first screw portion, wherein the rod is operatively arranged to displace the first screw portion and the second screw portion toward each other.

In some embodiments, the first screw portion further comprises threading arranged on the first radially outward facing surface, at least one flute extending from the first distal end to the first proximal end, and at least one cutting edge operatively arranged to cut through bone. In some embodiments, the first screw portion comprises a first flute including a first cutting edge, the first cutting edge arranged proximate the first distal end and arranged to cut when the first screw portion is displaced in a first circumferential direction, and a second flute including a second cutting edge, the second cutting edge arranged proximate the first proximal end and arranged to cut when the first screw portion is displaced in a second circumferential direction, opposite the first circumferential direction. In some embodiments, the second screw portion further comprises threading arranged on the second radially outward facing surface. In some embodiments, the fusion device assembly further comprises a second hole extending through the second screw portion and the bone graft section, the rod engaged with the second hole. In some embodiments, when the rod is displaced in a first circumferential direction the second screw portion and the section are displaced in a axial direction toward the first screw portion. In some embodiments, the first screw portion comprises a first diameter, the second screw portion comprises a second diameter, and the bone graft section comprises a third diameter, wherein the third diameter is less than the first diameter and the second diameter. In some embodiments, an overall length of the fusion device assembly is adjustable via the rod.

According to aspects illustrated herein, there is provided a fusion device assembly for fusion of a bone structure or joint, comprising a first screw portion, including a first distal end, a first proximal end, a first hole, a first radially outward facing surface, including a first threading, a first flute including a first cutting edge, the first cutting edge arranged proximate the first distal end and arranged to cut when the first screw portion is displaced in a first circumferential direction, and a second flute including a second cutting edge, the second cutting edge arranged proximate the first proximal end and arranged to cut when the first screw portion is displaced in a second circumferential direction, opposite the first circumferential direction, a second screw portion, including a second distal end, a second proximal end, and a second radially outward facing surface including a second threading, and a bone graft section, including a first end slidably engaged with the first hole, a second end non-rotatably secured to the second distal end, and a third radially outward facing surface.

In some embodiments, the bone material harvested by the cutting edge or edges of the tip are directed by one or more flutes to the slidable unthreaded segment of the screw or fusion device. Such bone drillings accumulate circumferentially around the unthreaded shaft component as a harvested autograft to be held and stored in that position for the purpose of fusion across a bone interface. Said graft is then capable being placed under compression according to Wolff's law by axial shortening of the unthreaded shaft component which in turn draws together the proximal and distal threaded segments of the screw or fusion device to manifest such compression of not only the harvested autograft, but also the proximate surfaces of the bone elements being fused.

These and other objects, features, and advantages of the present disclosure will become readily apparent upon a review of the following detailed description of the disclosure, in view of the drawings and appended claims.

BRIEF DESCRIPTION OF THE DRAWINGS

The accompanying drawings are incorporated herein as part of the specification. The drawings described herein illustrate embodiments of the presently disclosed subject matter and are illustrative of selected principles and teachings of the present disclosure, in which corresponding reference symbols indicate corresponding parts. However, the drawings do not illustrate all possible implementations of the presently disclosed subject matter and are not intended to limit the scope of the present disclosure in any way.

FIG. 5A is a front perspective view of the fusion device shown in FIG. 1.

FIG. 5B is a rear perspective view of the fusion device shown in FIG. 1.

FIG. 5C is a rear elevational view of the fusion device shown in FIG. 1.

FIG. 6 is a cross-sectional view of the fusion device taken generally along line 6-6 in FIG. 5A.

DETAILED DESCRIPTION

Figure 1:
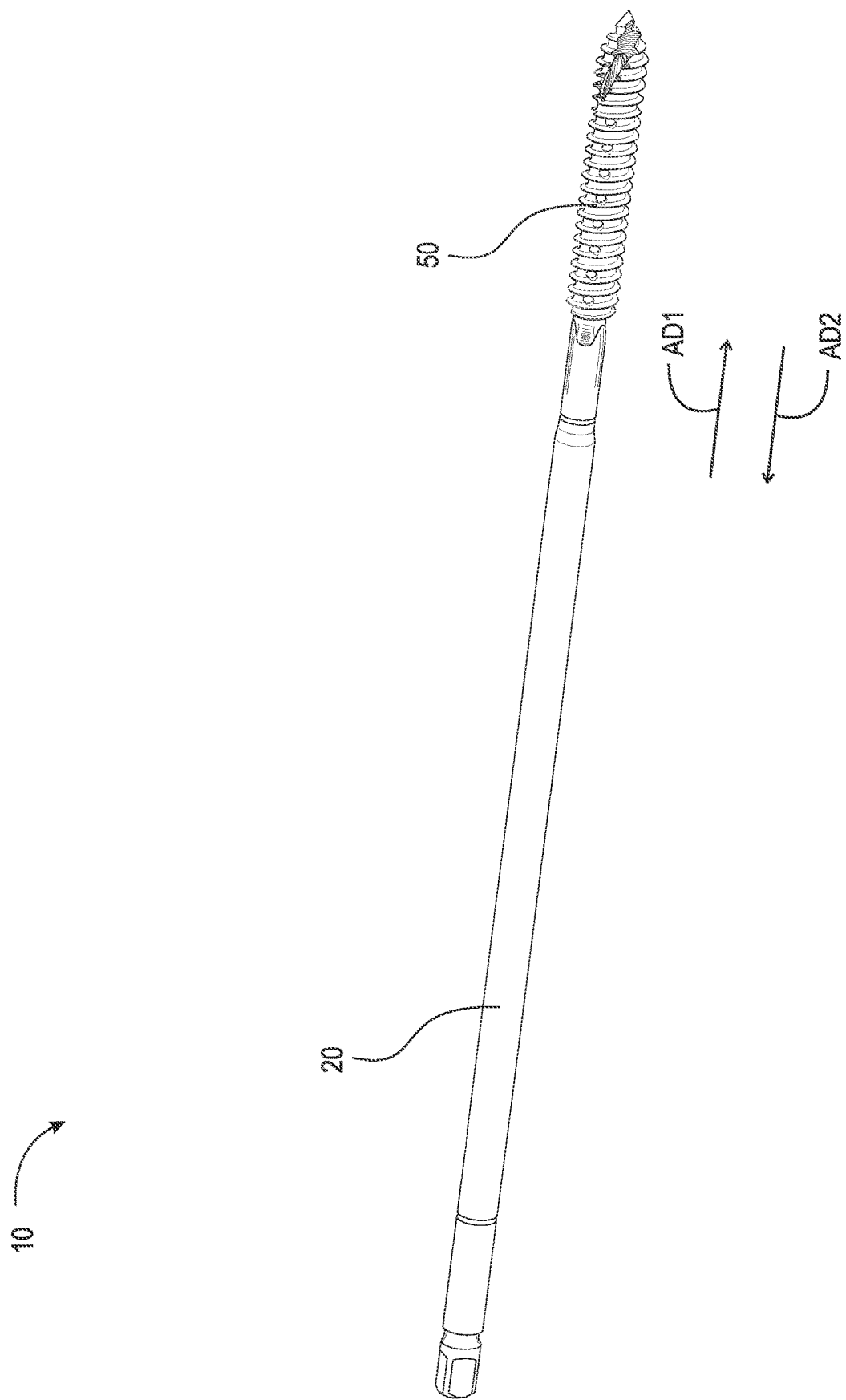
FIG. 1 is a front perspective view of a fusion device assembly.

At the outset, it should be appreciated that like drawing numbers on different drawing views identify identical, or functionally similar, structural elements. It is to be understood that the claims are not limited to the disclosed aspects.

Furthermore, it is understood that this disclosure is not limited to the particular methodology, materials and modifications described and as such may, of course, vary. It is also understood that the terminology used herein is for the purpose of describing particular aspects only, and is not intended to limit the scope of the claims.

Unless defined otherwise, all technical and scientific terms used herein have the same meaning as commonly understood to one of ordinary skill in the art to which this disclosure pertains. It should be understood that any methods, devices or materials similar or equivalent to those described herein can be used in the practice or testing of the example embodiments.

It should be appreciated that the term "substantially" is synonymous with terms such as "nearly," "very nearly," "about," "approximately," "around," "bordering on," "close to," "essentially," "in the neighborhood of," "in the vicinity of," etc., and such terms may be used interchangeably as appearing in the specification and claims. It should be appreciated that the term "proximate" is synonymous with terms such as "nearby," "close," "adjacent," "neighboring," "immediate," "adjoining," etc., and such terms may be used interchangeably as appearing in the specification and claims. The term "approximately" is intended to mean values within ten percent of the specified value.

It should be understood that use of "or" in the present application is with respect to a "non-exclusive" arrangement, unless stated otherwise. For example, when saying that "item x is A or B," it is understood that this can mean one of the following: (1) item x is only one or the other of A and B; (2) item x is both A and B. Alternately stated, the word "or" is not used to define an "exclusive or" arrangement. For example, an "exclusive or" arrangement for the statement "item x is A or B" would require that x can be only one of A and B. Furthermore, as used herein, "and/or" is intended to mean a grammatical conjunction used to indicate that one or more of the elements or conditions recited may be included or occur. For example, a device comprising a first element, a second element and/or a third element, is intended to be construed as any one of the following structural arrangements: a device comprising a first element; a device comprising a second element; a device comprising a third element; a device comprising a first element and a second element; a device comprising a first element and a third element; a device comprising a first element, a second element and a third element; or, a device comprising a second element and a third element.

Moreover, as used herein, the phrases "comprises at least one of" and "comprising at least one of" in combination with a system or element is intended to mean that the system or element includes one or more of the elements listed after the phrase. For example, a device comprising at least one of: a first element; a second element; and, a third element, is intended to be construed as any one of the following structural arrangements: a device comprising a first element; a device comprising a second element; a device comprising a third element; a device comprising a first element and a second element; a device comprising a first element and a third element; a device comprising a first element, a second element and a third element; or, a device comprising a second element and a third element. A similar interpretation is intended when the phrase "used in at least one of:" is used herein.

By "non-rotatably connected" elements, we mean that: the elements are connected so that whenever one of the elements rotate, all the elements rotate; and relative rotation between the elements is not possible. Radial and/or axial movement of non-rotatably connected elements with respect to each other is possible, but not required.

Figure 2:
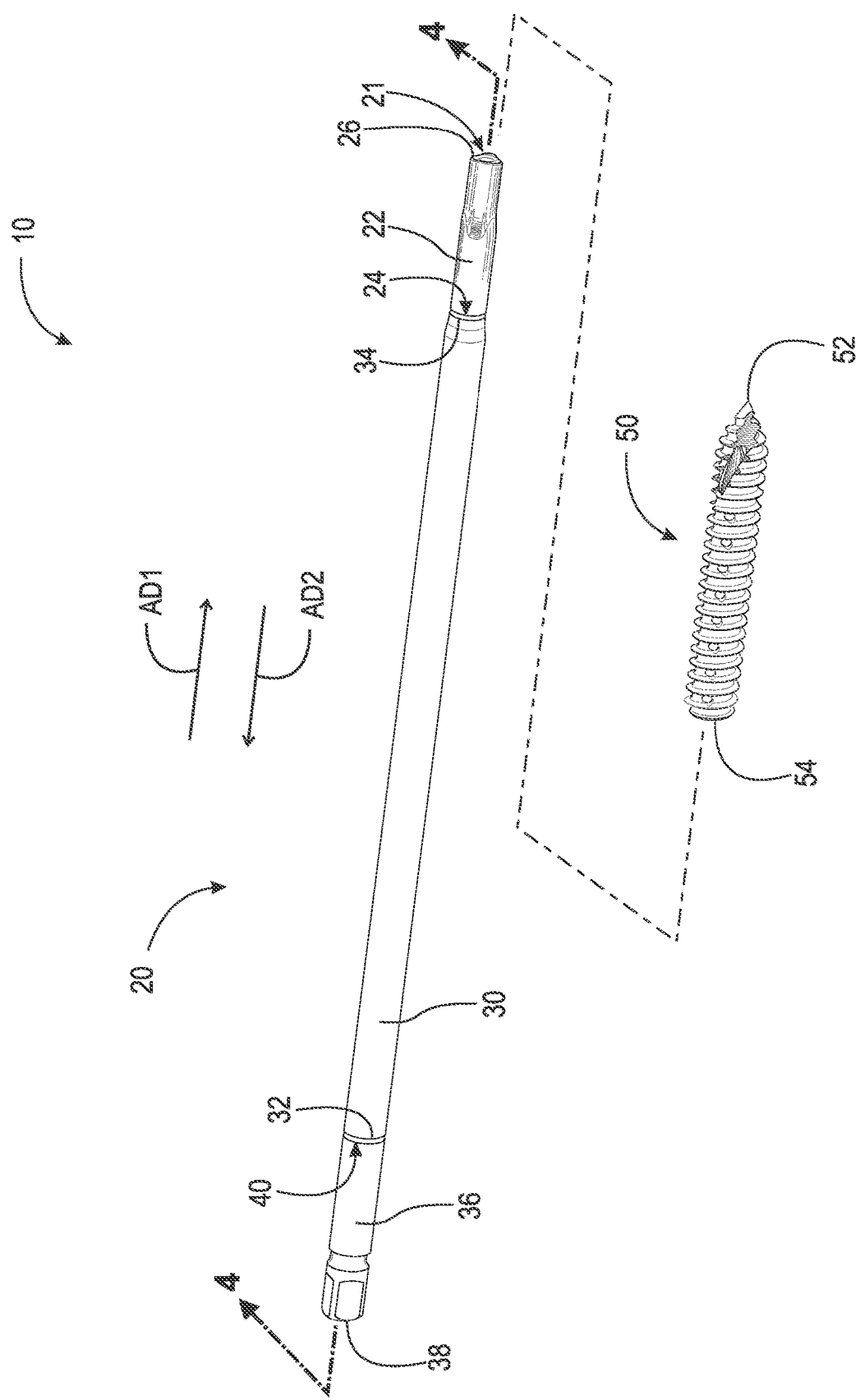
FIG. 2 is a front exploded perspective view of the fusion device assembly shown in FIG. 1.

Adverting now to the figures, FIG. 1 is a front perspective view of fusion device assembly 10. FIG. 2 is a front exploded perspective view of fusion device assembly 10. Fusion device assembly 10 generally comprises shaft 20 and fusion device 50. It should be appreciated that fusion devices 150 and 250 are also compatible with shaft 20 and may form fusion device assembly 10 along therewith. Shaft 20 is operatively arranged to drive fusion device 50 (and fusion devices 150 and 250) into a joint and allow graft material to be injected therein, as will be described in greater detail below.

Figure 3:
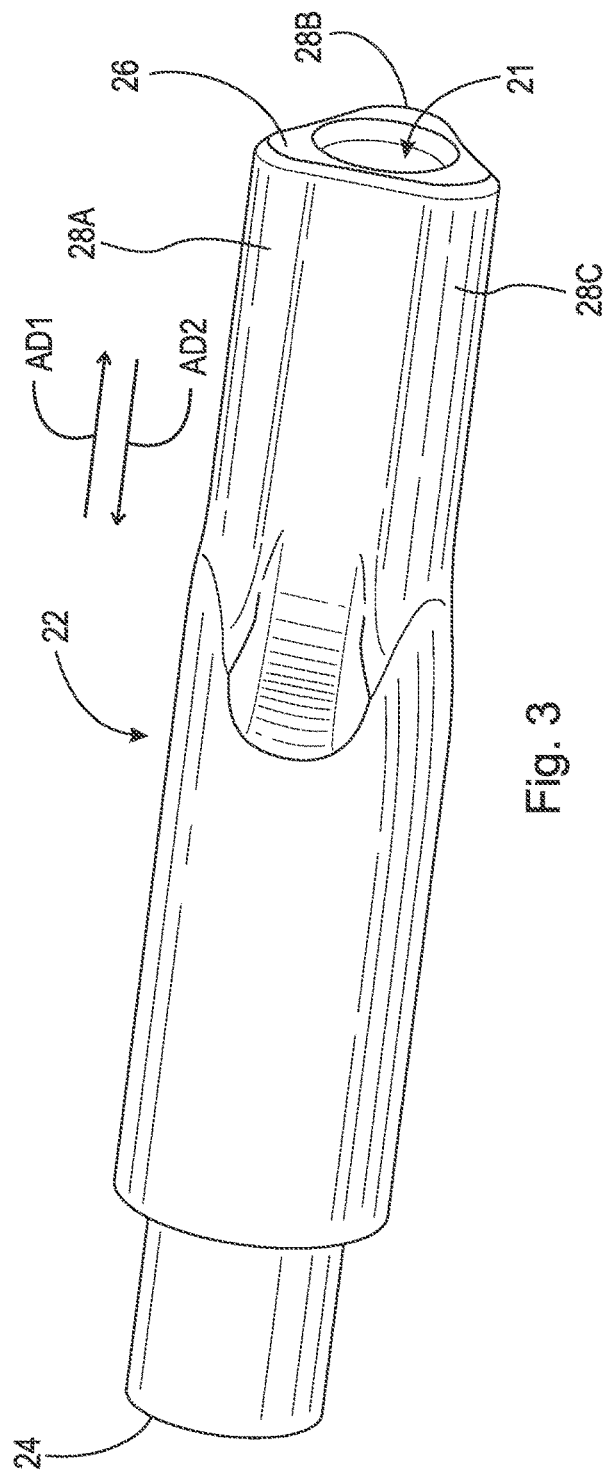
FIG. 3 is a front perspective view of a section of the shaft shown in FIG. 1.
Figure 4:
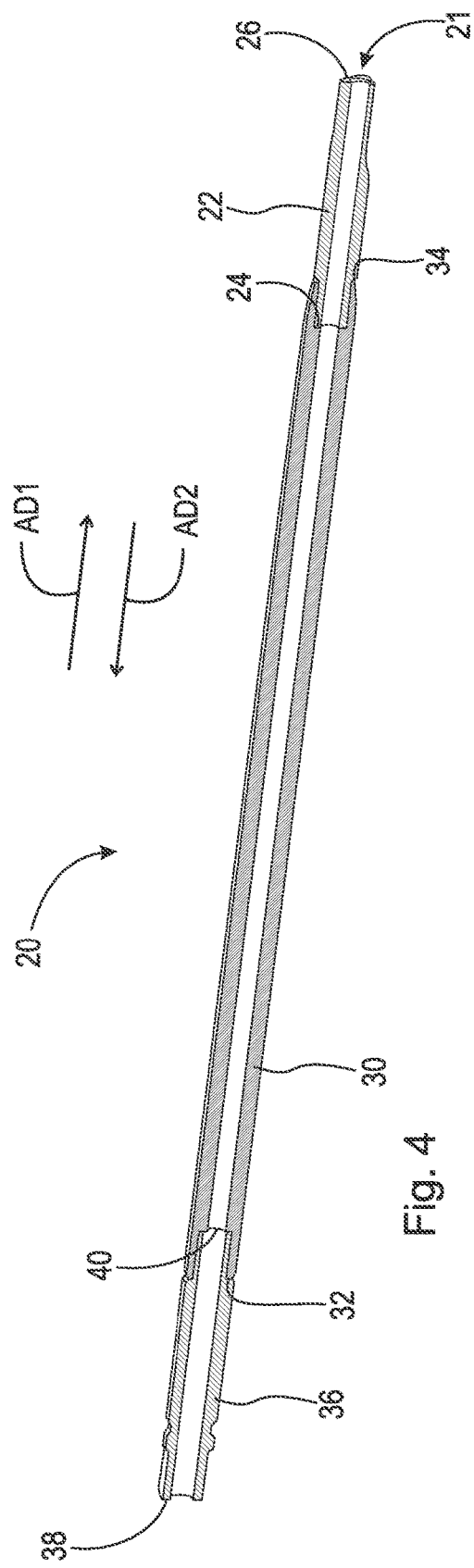
FIG. 4 is a cross-sectional view of the shaft taken generally along line 4-4 in FIG. 2.

FIG. 3 is a front perspective view of a section of shaft 20. FIG. 4 is a cross-sectional view of shaft 20 taken generally along line 4-4 in FIG. 2.

Shaft 20 generally comprises through-bore 21, end 26, and end 32. Through-bore 21 extends from end 26 through end 32. In some embodiments, through-bore 21 extends from end 26 through end 38. In some embodiments, shaft 20 comprises one or more sections (e.g., sections 22, 30, and 36).

Section 22 is generally cylindrical and comprises end 24 and end 26. End 26 includes a coupler to non-rotatably connect shaft 20 to fusion device 50, 150, 250. For example, end 26 may comprise coupling lobes 28A-C that engage coupling lobes 56A-C in fusion device 50, similar to a socket connection, to non-rotatably connect shaft 20 and fusion device 50. In some embodiments, section 22 is removably connected to section 30, such that various coupler sizes or geometries may be assembled on shaft 20.

Section 30 is generally cylindrical and comprises end 32 and end 34. End 34 is arranged to engage end 24 to non-rotatably connect sections 22 and 30. End 32 is arranged to engage end 40 to non-rotatably connect sections 30 and 36.

Section 36 comprises end 38 and end 40. In some embodiments, section 36 is a hollow cylinder. In such embodiments, bone graft material can be inserted into end 38 and injected into fusion device 50, 150, 250 through through-bore 21. In some embodiments, section 36 is solid and is removably connected to section 30. In such embodiments, section 36 can be removed from section 30 such that bone graft material can be inserted into end 32 and injected into fusion device 50, 150, 250 through through-bore 21. End 40 is arranged to engage end 32 to non-rotatably connect sections 30 and 36. End 38 may comprise a universal coupler for connection to tool 12 (see FIGS. 17-18), for example, a power drill, torque handle, ratcheting T-handle, etc. In some embodiments, end 38 is a universal hex bit. In some embodiments, end 38 is a universal square bit.

Shaft 20 is specifically designed to circumferentially drive fusion device 50, 150, 250 into a joint. Once fusion device 50, 150, 250 is properly implanted, bone graft material is then injected into fusion device 50, 150, 250 through shaft 20, specifically through through-bore 21. As previously described, in some embodiments, section 36 is first removed to inject bone material through shaft 20. A plunger or a ram rod may be employed to force the bone graft material through shaft 20 and into fusion device 50, 150, 250. For example, a small rod having a diameter that is less than the diameter of through-bore 21 may be inserted into through-bore 21, after the bone graft material, to inject or pack the bone graft material into fusion device 50, 150, 250, similar to a ram rod of a musket. In some embodiments, bone material is inserted into shaft 20 through end 38. It should be appreciated that in some embodiments, shaft 20 is a single element (i.e., sections 22, 30, and 36 are integrally formed).

FIG. 5A is a front perspective view of fusion device 50. FIG. 5B is a rear perspective view of fusion device 50. FIG. 5C is a rear elevational view of fusion device 50. FIG. 6 is a cross-sectional view of fusion device 50 taken generally along line 6-6 in FIG. 5A. Fusion device 50 generally comprises bore 51, end 52, end 54, and radially outward facing surface 58.

Fusion device 50 is generally cylindrical and is operatively arranged to engage a joint. Fusion device 50 is a self-boring, self-tapping, fusion screw. In some embodiments, fusion device 50 is hollow and self-harvesting (i.e., harvests bone). As shown, fusion device 50 comprises a twist bit, a multi-purpose bit, or a pilot point bit having a cutting point/tip/edge, i.e., drill bit 53, at end 52, which comprises one or more flutes 64. Flutes 64 may comprise one or more cutting edges. In some embodiments, end 52 comprises a Brad point bit, a Forstner bit, or a spade bit. End 52 and flutes 64 are operatively arranged to bore a hole through the joint, specifically through the bone. Fusion device 50 further comprises one or more apertures 66 formed adjacent to flutes 64. Flutes 64 and apertures 66 work in conjunction such that as fusion device 50 is being driven into the joint, bone is removed from the joint by the tip at end 52 and flutes 64 and forced into bore 51 via apertures 66. The removed bone that is forced into bore 51 aids in the fusion of the joint. Bore 51 extends substantially through fusion device 50. Specifically, bore 51 extends from end 54 to proximate end 52. Apertures 66 extend from radially outward facing surface 58 radially inward to bore 51. End 54 includes a coupler to non-rotatably connect shaft 20 to fusion device 50. For example, end 54 may comprise coupling lobes 56A-C that engage coupling lobes 28A-C in shaft 20, similar to a socket connection, to non-rotatably connect shaft 20 and fusion device 50 (see FIG. 5C). Radially outward facing surface 58 further comprises threading 60. Threading 60 is designed not only to secure the joint (two bones) together, but also to tap the hole bored out in the joint by end 52 (the drill tip) and flutes 64. In some embodiments, threading 60 comprises a varying pitch such that compression occurs gradually across the joint as fusion device 50 advances therein. In some embodiments, radially outward facing surface 58 comprises threading from end 52 to end 54 (i.e., fusion device 50 is fully threaded). In some embodiments, radially outward facing surface 58 is partially threaded. For example, threads and flutes are found proximate end 52 followed by a non-threaded middle section and then smaller pitched threads proximate end 54 to facilitate joint compression in the manner of a lag-screw. In some embodiments, fusion device 50 is a fully threaded regular pitch bone screw. Radially outward facing surface 58 further comprises a plurality of apertures 62. Apertures 62 extend from radially outward facing surface 58 radially inward to bore 51 and allow for the removed bone material residing in bore 51 (i.e., the bone material fed into bore 51 through apertures 66) to engage with the joint such that, over time, joint fusion occurs. Apertures 62 further allow for bone graft material injected into fusion device 50 through shaft 20 to engage the joint for joint fusion. In other words, apertures 62 allow for bony in-growth and through growth/fusion. It should be appreciated that apertures 62 may comprise any geometric shape suitable to allow fusion to occur between graft residing within bore 51 and the joint (e.g., circular, ovular, triangular, square, rectangular, etc.).

Figure 7:
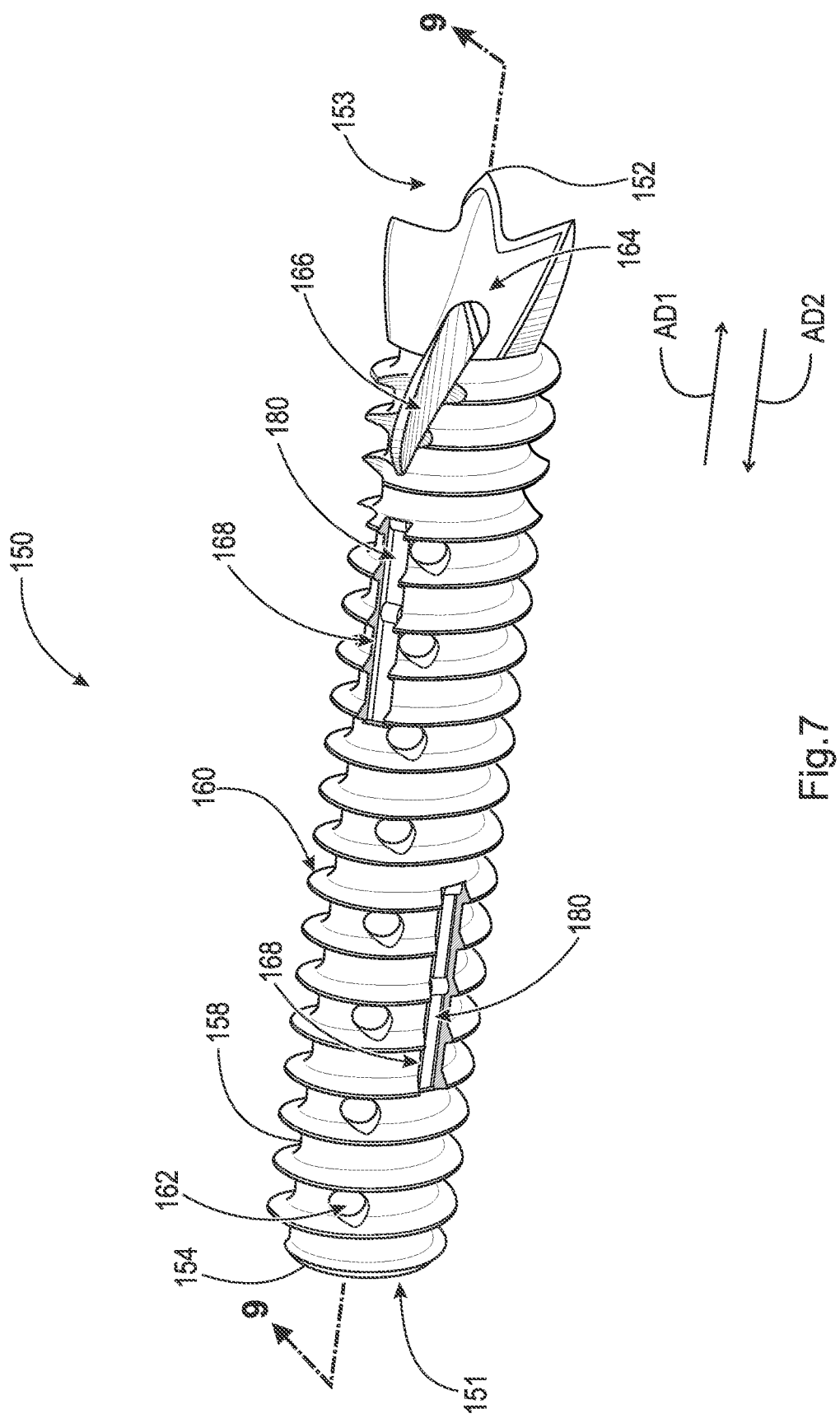
FIG. 7 is a front perspective view of a fusion device, in an unexpanded state.
Figure 8:
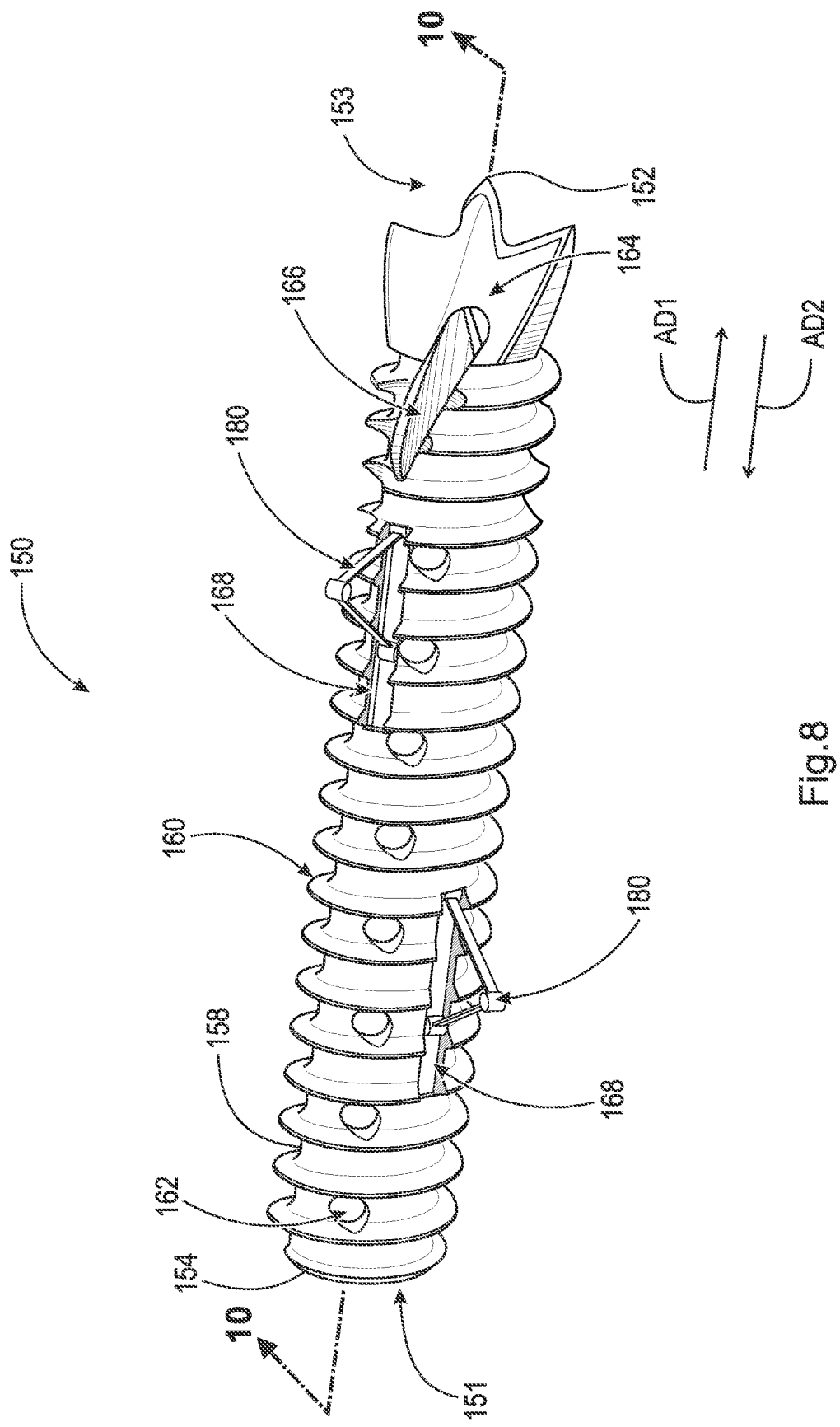
FIG. 8 is a front perspective view of the fusion device shown in FIG. 7, in an expanded state.
Figure 9:
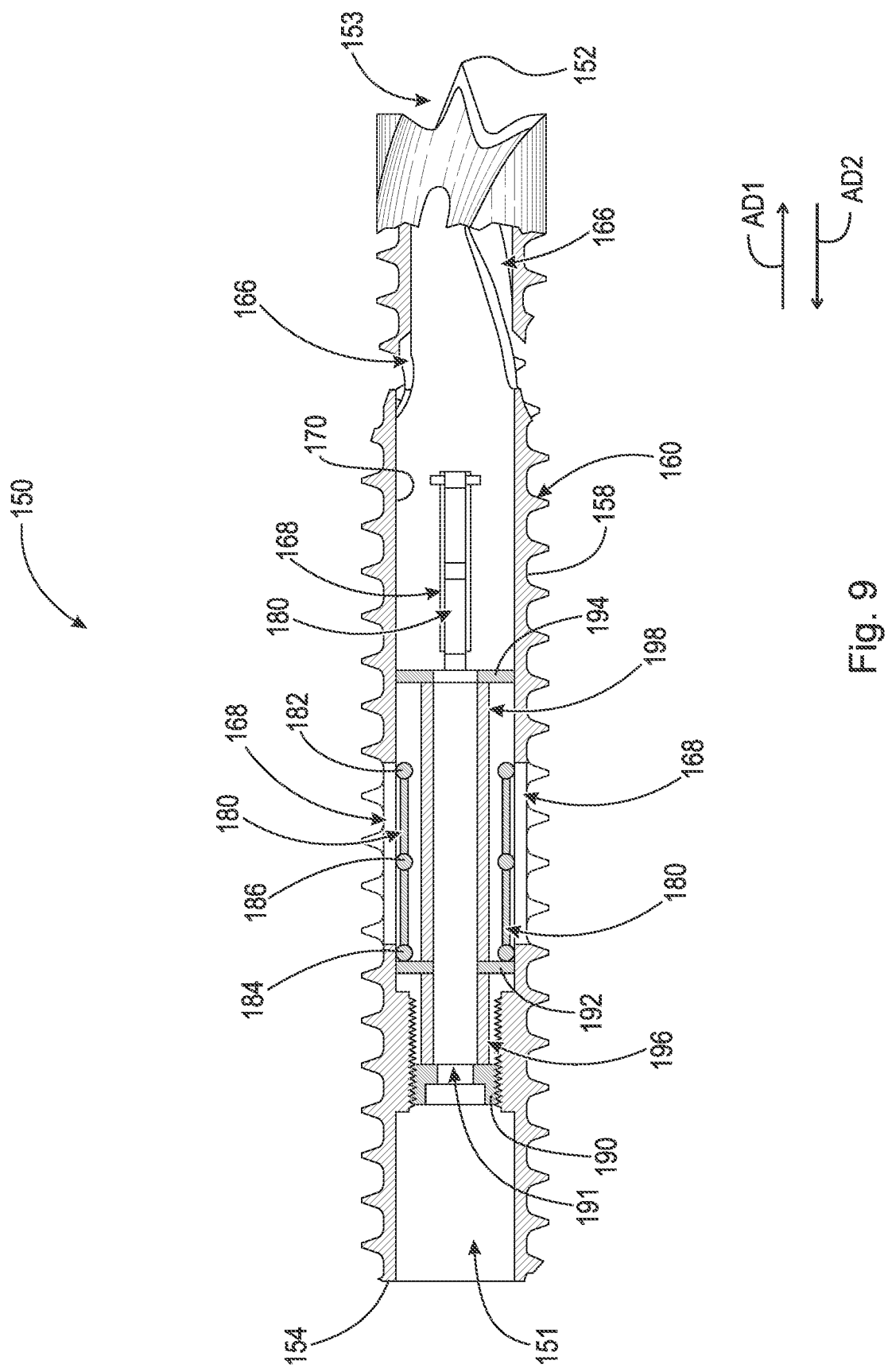
FIG. 9 is a cross-sectional view of the fusion device, in the unexpanded state, taken generally along line 9-9 in FIG. 7.
Figure 10:
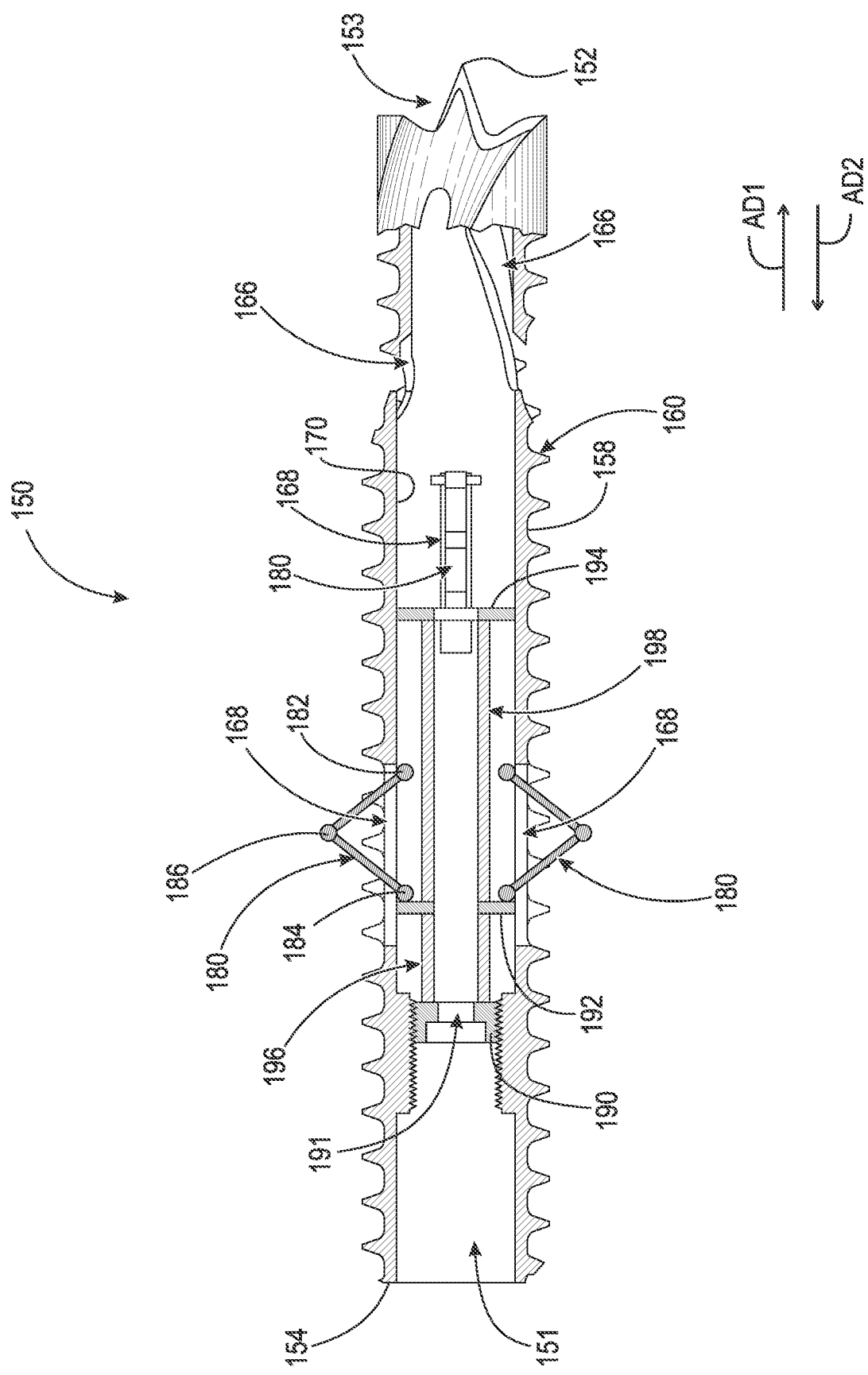
FIG. 10 is a cross-sectional view of the fusion device, in the expanded state, taken generally along line 10-10 in FIG. 8.
Figure 11:
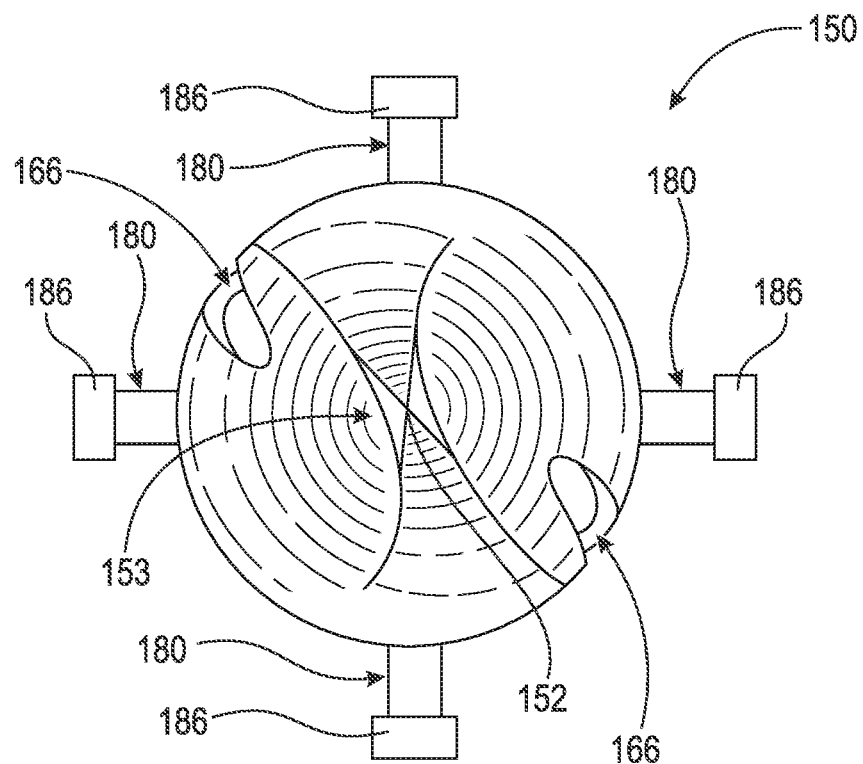
FIG. 11 is a front elevational view of the fusion device, in the expanded state, shown in FIG. 8.
Figure 12:
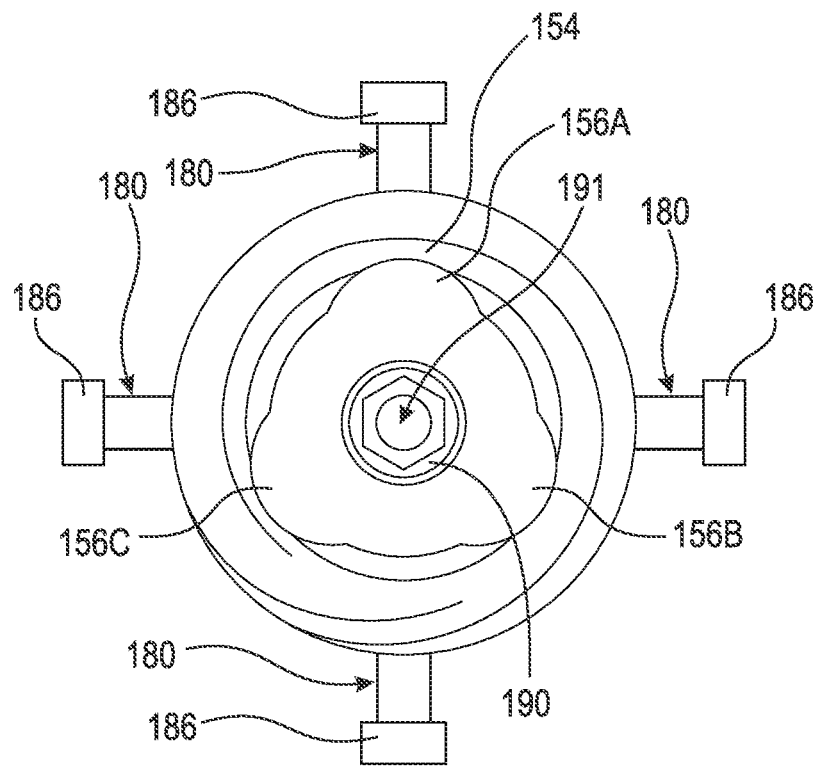
FIG. 12 is a rear elevational view of the fusion device, in the expanded state, shown in FIG. 8.

FIG. 7 is a front perspective view of fusion device 150, in an unexpanded state. FIG. 8 is a front perspective view of fusion device 150, in an expanded state. FIG. 9 is a cross-sectional view of fusion device 150, in the unexpanded state, taken generally along line 9-9 in FIG. 7. FIG. 10 is a cross-sectional view of fusion device 150, in the expanded state, taken generally along line 10-10 in FIG. 8. FIG. 11 is a front elevational view of fusion device 150, in the expanded state. FIG. 12 is a rear elevational view of fusion device 150, in the expanded state. Fusion device 150 generally comprises bore 151, end 152, end 154, and radially outward facing surface 158.

Fusion device 150 is generally cylindrical and is operatively arranged to engage a joint. Fusion device 150 is a self-boring, self-tapping, fusion screw. In some embodiments, fusion device 150 is hollow and self-harvesting (i.e., harvests bone). As shown, fusion device 150 comprises a Brad point bit having a cutting point/tip/edge, i.e., drill bit 153, at end 152, which comprises one or more flutes 164. Flutes 164 may comprise one or more cutting edges. In some embodiments, end 152 comprises a twist bit, a multi-purpose bit, a pilot point bit, a Forstner bit, or a spade bit. End 152 and flutes 164 are operatively arranged to bore a hole through the joint, specifically through the bone. Fusion device 150 further comprises one or more apertures 166 formed adjacent to flutes 164. Flutes 164 and apertures 166 work in conjunction such that as fusion device 150 is being driven into the joint, bone is removed from the joint by the tip at end 152 and flutes 164 and forced into bore 151 via apertures 166. The removed bone that is forced into bore 151 aids in the fusion of the joint. Bore 151 extends substantially through fusion device 150. Specifically, bore 151 extends from end 154 to proximate end 152. Apertures 166 extend from radially outward facing surface 158 radially inward to bore 151. End 154 includes a coupler to non-rotatably connect shaft 20 to fusion device 150. For example, end 154 may comprise coupling lobes 156A-C that engage coupling lobes 28A-C in shaft 20, similar to a socket connection, to non-rotatably connect shaft 20 and fusion device 150 (see FIG. 12). Radially outward facing surface 158 further comprises threading 160. Threading 160 is designed not only to secure the joint (two bones) together, but also to tap the hole bored out in the joint by end 152 (the drill tip) and flutes 164. In some embodiments, threading 160 comprises a varying pitch such that compression occurs gradually across the joint as fusion device 150 advances therein. In some embodiments, radially outward facing surface 158 comprises threading from end 152 to end 154 (i.e., fusion device 150 is fully threaded). In some embodiments, radially outward facing surface 158 is partially threaded. For example, threads and flutes are found proximate end 152 followed by a non-threaded middle section and then smaller pitched threads proximate end 154 to facilitate joint compression in the manner of a lag-screw. In some embodiments, fusion device 150 is a fully threaded regular pitch bone screw. Radially outward facing surface 158 further comprises a plurality of apertures 162. Apertures 162 extend from radially outward facing surface 158 radially inward to bore 151 and allow for the removed bone material residing in bore 151 (i.e., the bone material fed into bore 151 through apertures 166) to engage with the joint such that, over time, joint fusion occurs. Apertures 162 further allow for bone graft material injected into fusion device 150 through shaft 20 to engage the joint for joint fusion. In other words, apertures 162 allow for bony in-growth and through growth/fusion. It should be appreciated that apertures 162 may comprise any geometric shape suitable to allow fusion to occur between graft residing within bore 151 and the joint (e.g., circular, ovular, triangular, square, rectangular, etc.).

Fusion device 150 further comprises one or more expandable members 180 operatively arranged to expand radially outward through one or more openings 168 from bore 151 and engage the bone(s) of the joint. As shown openings 168 are arranged in radially outward facing surface 158 and extend radially inward to bore 151. In some embodiments, expandable members 180 comprise pivots 182, 184, and 186. For example, pivot 182 may be fixedly secured to radially inward facing surface 170 and pivot 184 may be slidably connected to radially inward facing surface. As sliding pivot 184 is displaced in axial direction AD1, pivot 186 expands radially outward through openings 168 (see FIGS. 9-10). As expandable members 180 (e.g., radially expanding pivots 186) expand radially outward, they engage the joint or bones of the joint and prevent fusion device 150 from disengaging the joint (i.e., from unscrewing from the joint), and also serves to stabilize proximate elements of the bones or joint such that excess motion which may hinder fusion is thereby mitigated.

In some embodiments fusion device 150 further comprises nut 190 and one or more plates (e.g., plates 192 and 194) operatively arranged to displace pivot 184 in axial direction AD1 such that expandable members 180 expand radially through openings 168. Nut 190 is threadably engaged with radially inward facing surface 170 and comprises through-bore 191. Nut 190 is connected to plate 192 and/or plate 194 via one or more connectors 196 and/or one or more connectors 198, respectively. In some embodiments, nut 190 is non-rotatably connected to plate 192 and/or plate 194. In some embodiments, nut 190 is rotatably connected to plate 192 and/or plate 194. Plate 192 and plate 194 are operatively arranged to engage or abut against sliding pivots 184 to displace sliding pivots 184 in axial direction AD1. In some embodiments, nut 190 directly engages or abuts against sliding pivot 184 without the need for plates or connectors. Once fusion device 150 is properly implanted in a joint, shaft 20 is removed from end 154 and a tool (e.g., screwdriver, Allen wrench, socket, etc.) is inserted into nut 190. Nut 190 is rotated such that nut 190 is displaced in axial direction AD1 relative to end 154. This causes plates 192 and 194 and sliding pivots 184 to displace in axial direction AD1, which forces expandable members 180 radially outward through openings 168 to engage the bones of the joint. Through-bore 191 allows bone graft material to be injected into fusion device 150 through end 154 via shaft 20. In some embodiments, plate 192 comprises a through-bore. In some embodiments, plate 194 comprises a through-bore. In some embodiments, plate 192 and/or plate 194 is threadably engaged with radially inward facing surface 170.

Figure 13:
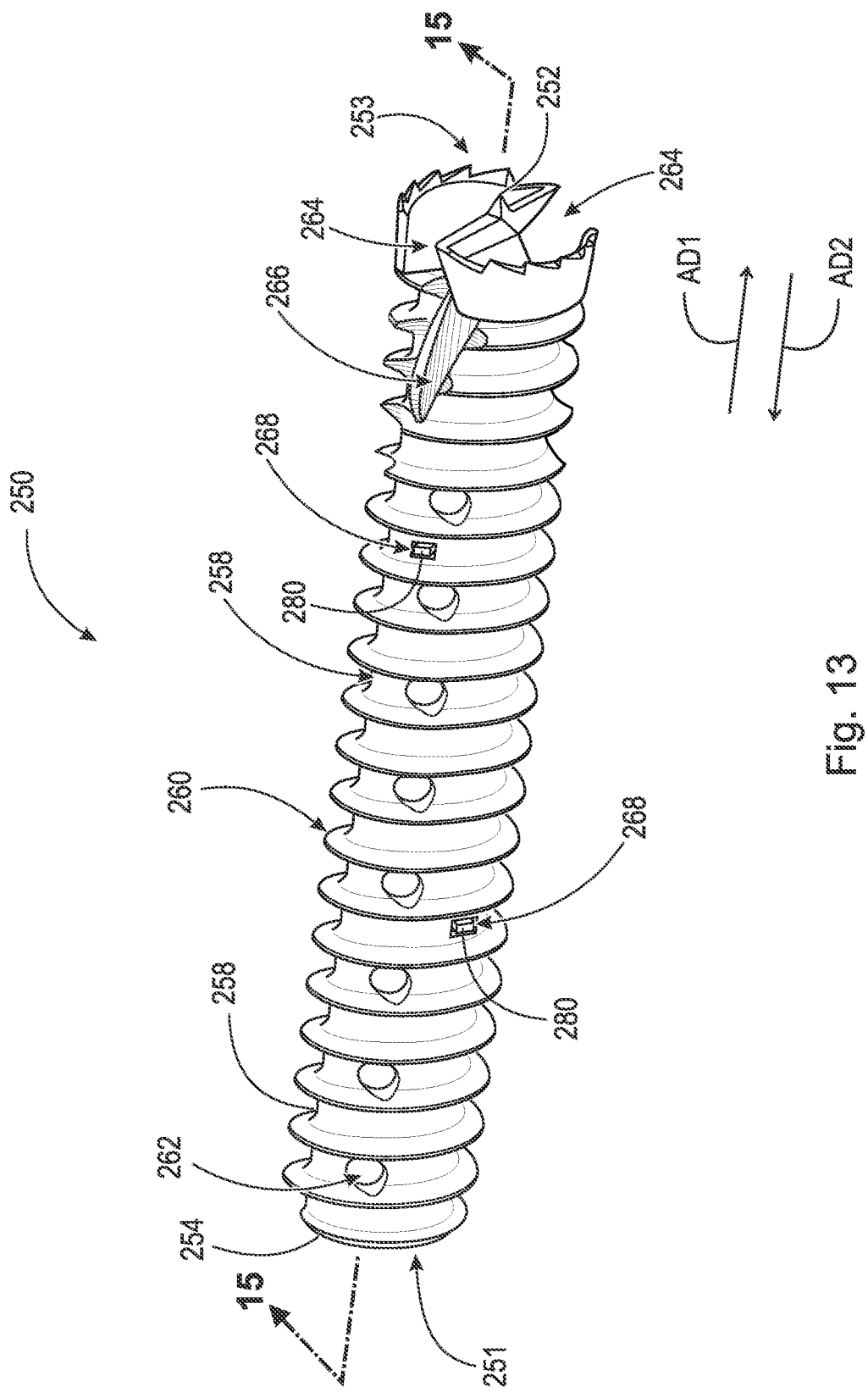
FIG. 13 is a front elevational view of a fusion device, in an unexpanded state.
Figure 14:
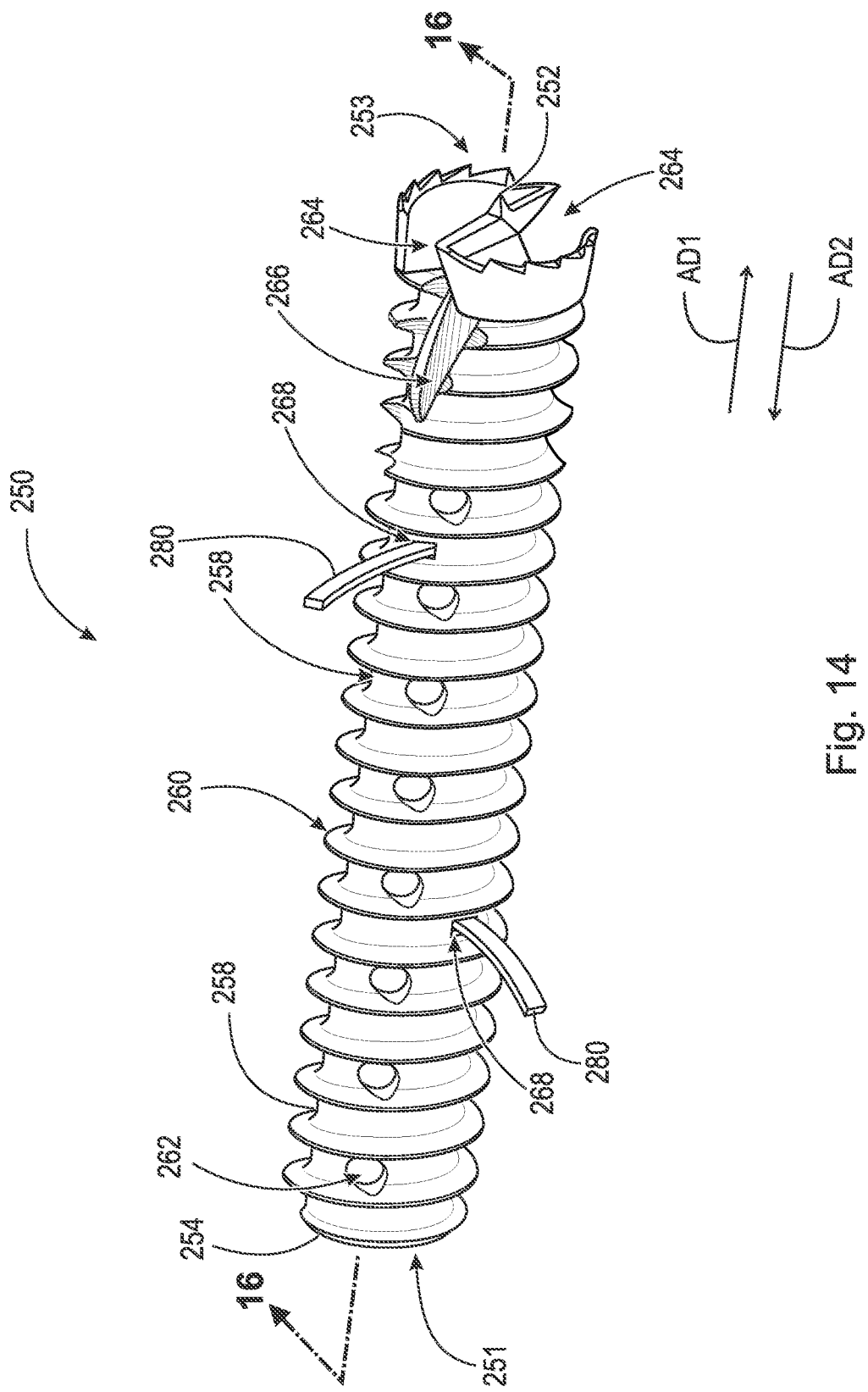
FIG. 14 is a front elevational view of the fusion device shown in FIG. 13, in an expanded state.
Figure 15:
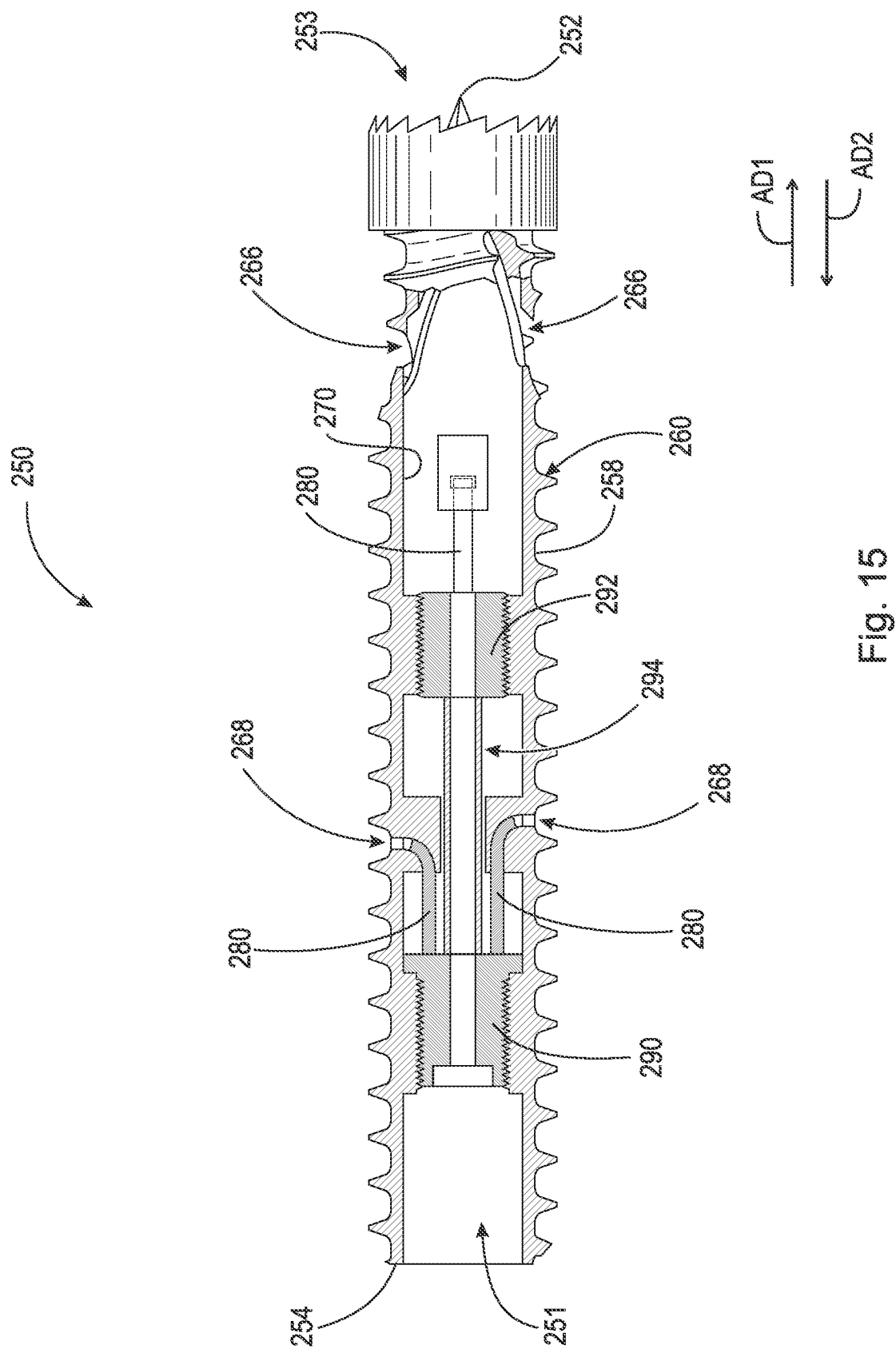
FIG. 15 is a cross-sectional view of the fusion device, in the unexpanded state, taken generally along line 15-15 in FIG. 13.
Figure 16:
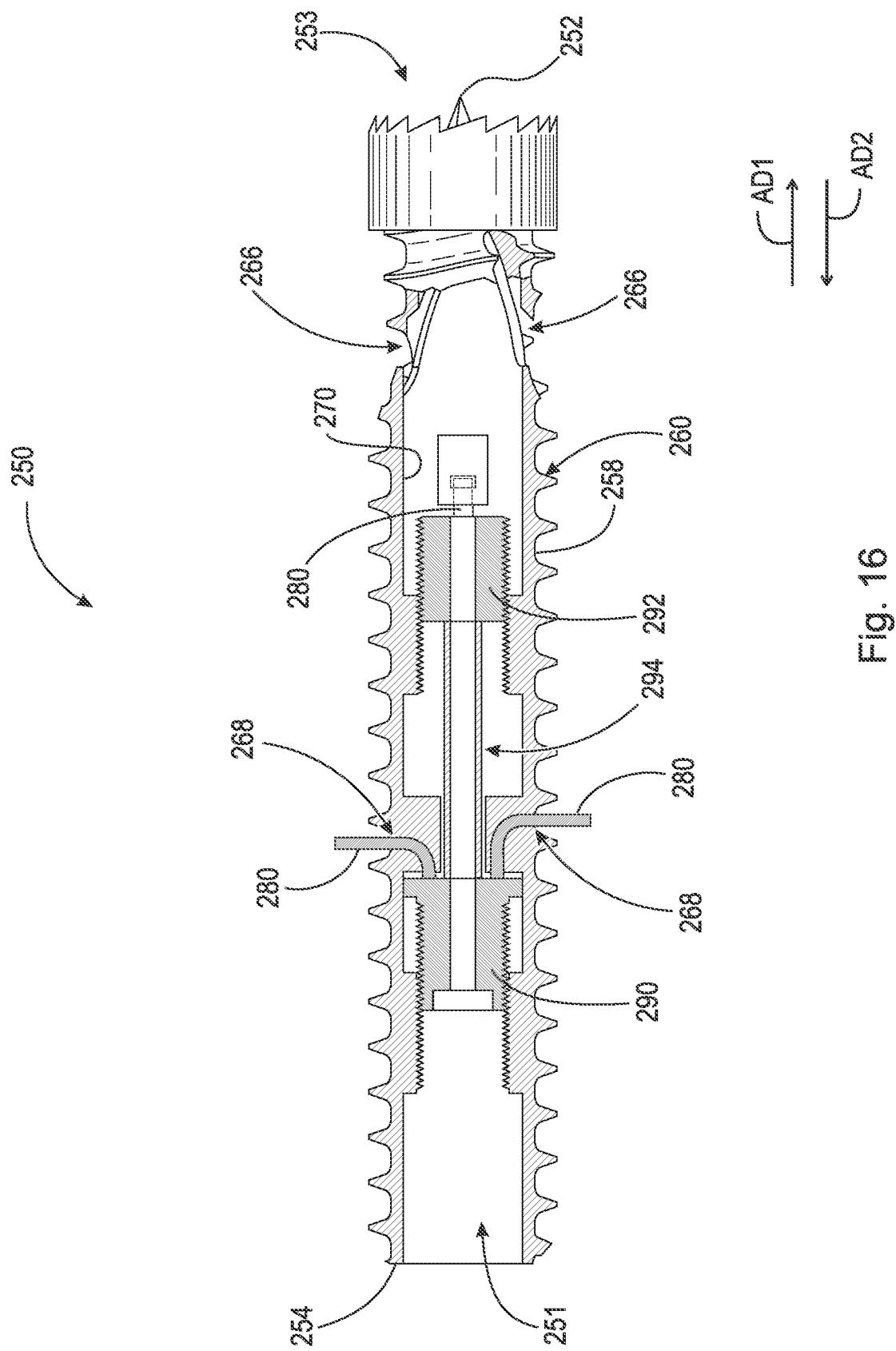
FIG. 16 is a cross-sectional view of the fusion device, in the expanded state, taken generally along line 16-16 in FIG. 14.

FIG. 13 is a front elevational view of fusion device 250, in an unexpanded state. FIG. 14 is a front elevational view of fusion device shown 250, in an expanded state. FIG. 15 is a cross-sectional view of fusion device 250, in the unexpanded state, taken generally along line 15-15 in FIG. 13. FIG. 16 is a cross-sectional view of fusion device 250, in the expanded state, taken generally along line 16-16 in FIG. 14. Fusion device 250 generally comprises bore 251, end 252, end 254, and radially outward facing surface 258.

Fusion device 150 is generally cylindrical and is operatively arranged to engage a joint. Fusion device 250 is a self-boring, self-tapping, fusion screw. In some embodiments, fusion device 250 is hollow and self-harvesting (i.e., harvests bone). As shown, fusion device 250 comprises a Forstner bit having a cutting point/tip/edge, i.e., drill bit 253, at end 252, which comprises one or more flutes 264. Flutes 264 may comprise one or more cutting edges. In some embodiments, end 252 comprises a twist bit, a multi-purpose bit, a pilot point bit, a Brad point bit, or a spade bit. End 252 and flutes 264 are operatively arranged to bore a hole through the joint, specifically through the bone. Fusion device 250 further comprises one or more apertures 266 formed adjacent to flutes 264. Flutes 264 and apertures 266 work in conjunction such that as fusion device 250 is being driven into the joint, bone is removed from the joint by the tip at end 252 and flutes 264 and forced into bore 251 via apertures 266. The removed bone that is forced into bore 251 aids in the fusion of the joint. Bore 251 extends substantially through fusion device 250. Specifically, bore 251 extends from end 254 to proximate end 252. Apertures 266 extend from radially outward facing surface 258 radially inward to bore 251. End 254 includes a coupler to non-rotatably connect shaft 20 to fusion device 250. For example, end 254 may comprise coupling lobes 256A-C (not shown) that engage coupling lobes 28A-C in shaft 20, similar to a socket connection, to non-rotatably connect shaft 20 and fusion device 250. Radially outward facing surface 258 further comprises threading 260. Threading 260 is designed not only to secure the joint (two bones) together, but also to tap the hole bored out in the joint by end 252 (the drill tip) and flutes 264. In some embodiments, threading 260 comprises a varying pitch such that compression occurs gradually across the joint as fusion device 250 advances therein. In some embodiments, radially outward facing surface 258 comprises threading from end 252 to end 254 (i.e., fusion device 250 is fully threaded). In some embodiments, radially outward facing surface 258 is partially threaded. For example, threads and flutes are found proximate end 252 followed by a non-threaded middle section and then smaller pitched threads proximate end 254 to facilitate joint compression in the manner of a lag-screw. In some embodiments, fusion device 250 is a fully threaded regular pitch bone screw. Radially outward facing surface 258 further comprises a plurality of apertures 262. Apertures 262 extend from radially outward facing surface 258 radially inward to bore 251 and allow for the removed bone material residing in bore 251 (i.e., the bone material fed into bore 251 through apertures 266) to engage with the joint such that, over time, joint fusion occurs. Apertures 262 further allow for bone graft material injected into fusion device 250 through shaft 20 to engage the joint for joint fusion. In other words, apertures 262 allow for bony in-growth and through growth/fusion. It should be appreciated that apertures 262 may comprise any geometric shape suitable to allow fusion to occur between graft residing within bore 251 and the joint (e.g., circular, ovular, triangular, square, rectangular, etc.).

Fusion device 250 further comprises one or more expandable members 280 operatively arranged to extend radially outward through one or more openings 268 from bore 251 and engage the bone(s) of the joint. As shown openings 268 are arranged in radially outward facing surface 258 and extend radially inward to bore 251. In some embodiments, expandable members 280 are flexible structures that can be fed along a curved path (FIGS. 15-16). As one end of expandable member 280 is displaced in axial direction AD1, the other end of expandable member 280 is curved radially outward from radially outward facing surface. As expandable members 280 extend radially outward, they engage the joint or bones of the joint and prevent fusion device 250 from disengaging the joint (i.e., from unscrewing from the joint).

In some embodiments fusion device 250 further comprises nut 290 and one or more plates (e.g., plate 292) operatively arranged to displace one end of expandable members 280 in axial direction AD1 such that the other end of expandable members 280 extends radially through openings 268. Nut 290 is threadably engaged with radially inward facing surface 270 and comprises through-bore 291. Nut 290 is connected to plate 292 via one or more connectors 294. In some embodiments, nut 290 is non-rotatably connected to plate 292. In some embodiments, nut 290 is rotatably connected to plate 292. Nut 290 and/or plate 292 is operatively arranged to engage or abut against expandable members 280 to displace expandable members 280 in axial direction AD1 (and subsequently radially outward from radially outward facing surface 258). In some embodiments, and as shown in FIGS. 15 and 16, nut 290 directly engages or abuts against expandable members 280. Once fusion device 250 is properly implanted in a joint, shaft 20 is removed from end 254 and a tool (e.g., screwdriver, Allen wrench, socket, etc.) is inserted into nut 290. Nut 290 is rotated such that nut 290 is displaced in axial direction AD1 relative to end 254. This causes plate 292 and one end of expandable members 280 to displace in axial direction AD1, which forces the other end of expandable members 280 radially outward through openings 268 to engage the bones of the joint. Through-bore 291 allows bone graft material to be injected into fusion device 250 through end 254 via shaft 20. In some embodiments, plate 292 comprises a through-bore. In some embodiments, plate 292 is threadably engaged with radially inward facing surface 270.

Figure 17:
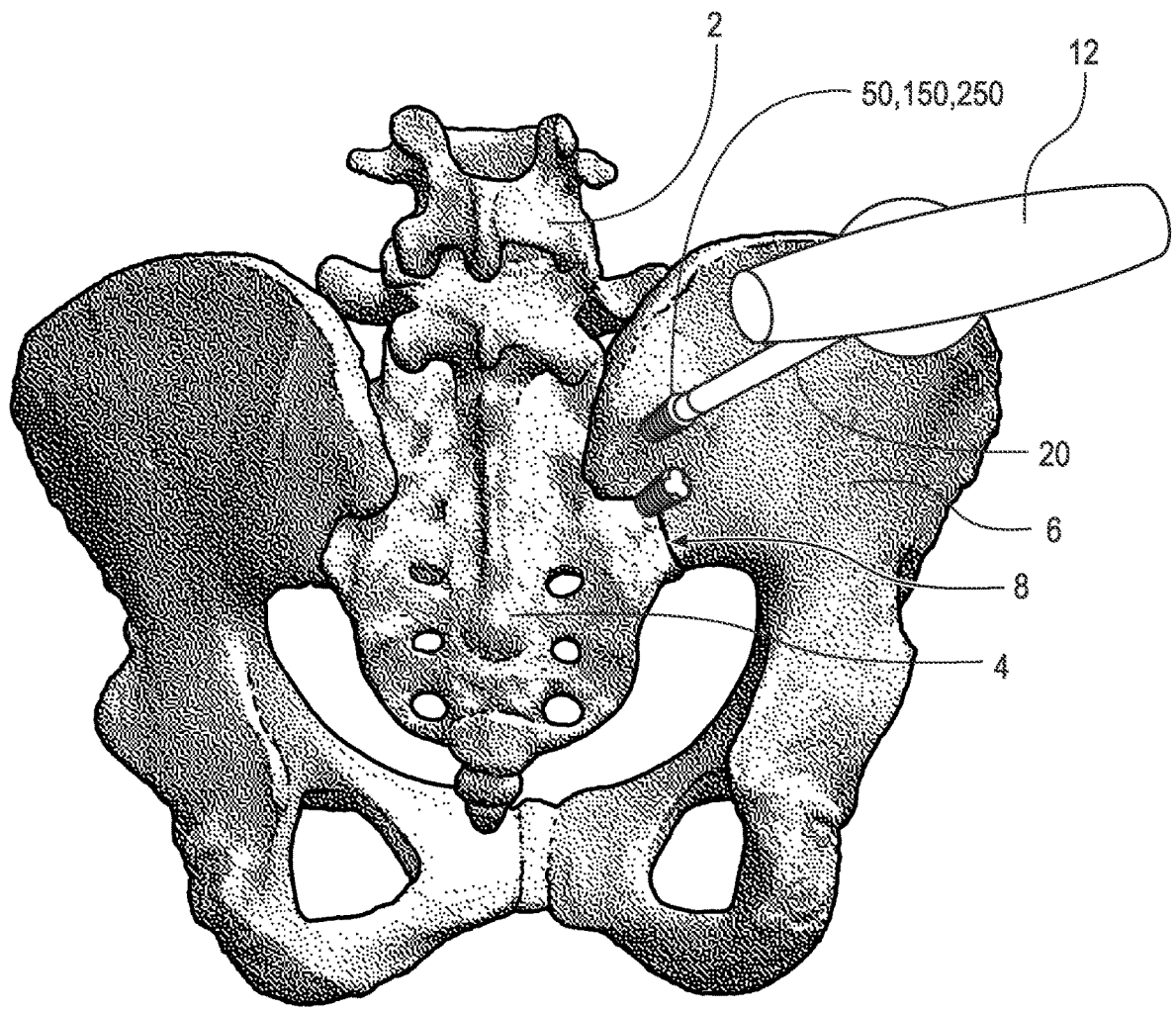
FIG. 17 is a posterior view of a fusion device being implanted in a sacroiliac joint.
Figure 18:
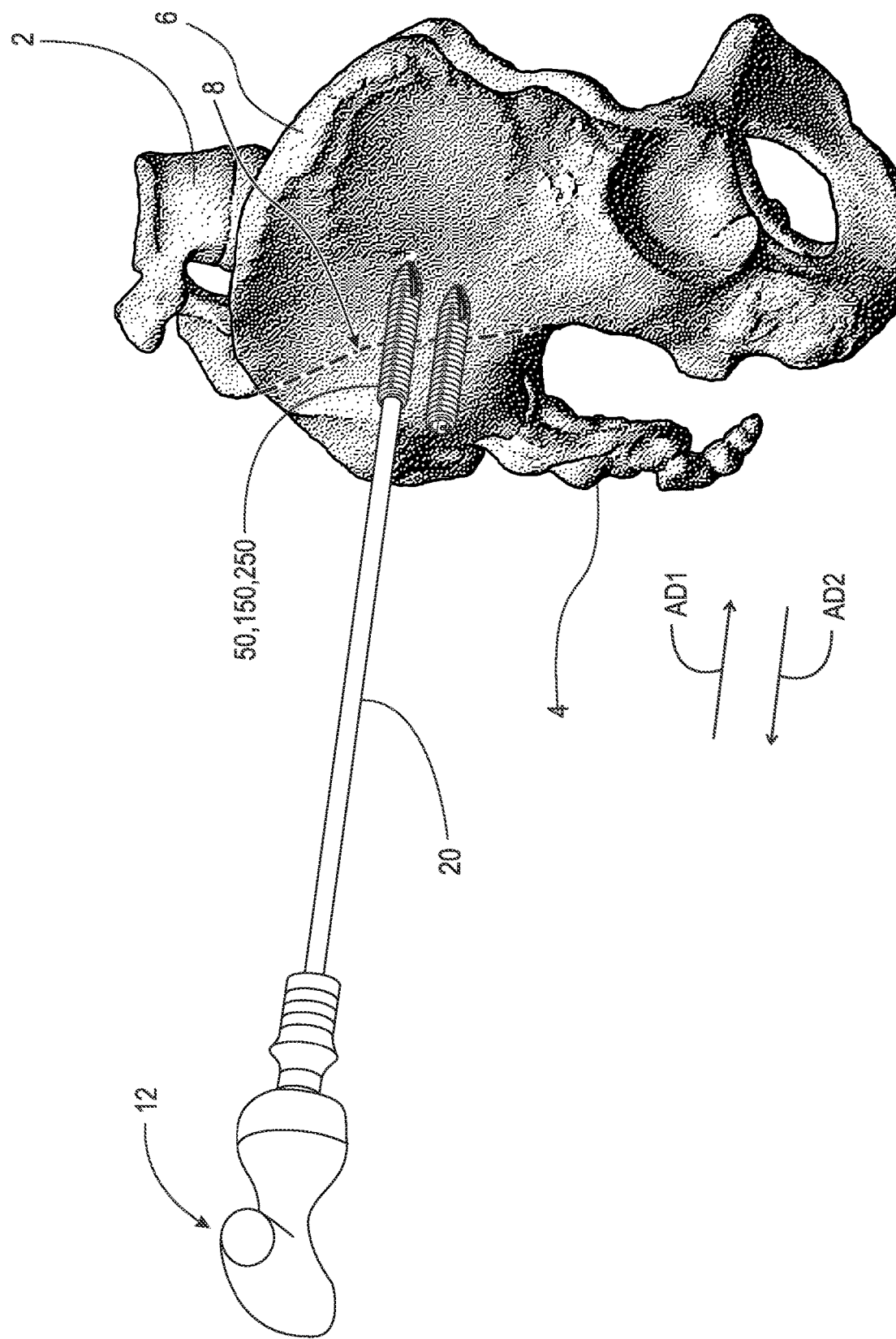
FIG. 18 is a lateral view of the fusion device being implanted in the sacroiliac joint, as shown in FIG. 17.

FIG. 17 is a posterior view of fusion device 50, 150, 250 being implanted in sacroiliac joint 8. FIG. 18 is a lateral view of fusion device 50, 150, 250 being implanted in sacroiliac joint 8. As shown, sacroiliac joint 8 comprises sacrum 4 and ilium 6. Sacrum 4 is connected to spinal column 2. Sacroiliac joint 8 is the connection between spinal column 2 and the pelvis. Fusion device 50, 150, 250 is implanted into sacroiliac joint 8 and once properly arranged, extends from ilium 6 to sacrum 4. As previously described, the threading of fusion device 50, 150, 250 is operatively arranged to pull ilium 6 and sacrum 4 together (i.e., into compression). Fusion device 50, 150, 250 is driven into sacroiliac joint 8 via shaft 20 and tool 12. In some embodiments, once fusion device 50, 150, 250 is in place, tool 12 is removed from shaft 20 and bone material is injected into fusion device 50, 150, 250 through shaft 20. Shaft 20 is then removed from fusion device 50, 150, 250 and the wound is closed. In some embodiments, shaft 20 is removed and expandable members within the fusion device (e.g., fusion device 150, 250) are expanded radially outward. For example, in fusion device 150, nut 190 is rotated such that expandable members 180 extend radially outward from radially outward surface 158 and engage sacrum 4 and/or ilium 6. In fusion device 250, nut 290 is rotated such that expandable members 280 extend radially outward from radially outward surface 258 and engage sacrum 4 and/or ilium 6. After radial expansion of fusion device 150, 250, shaft 20 can be reconnected thereto and bone graft material injected therein. Fusion device 50, 150, 250 left in situ once filled with fusion material. Fusion device 50, 150, 250 is shown being implanted into sacroiliac joint 8 posteriorly; however, it should be appreciated that fusion device 50, 150, 250 may be implanted into sacroiliac joint 8 laterally.

Figure 19:
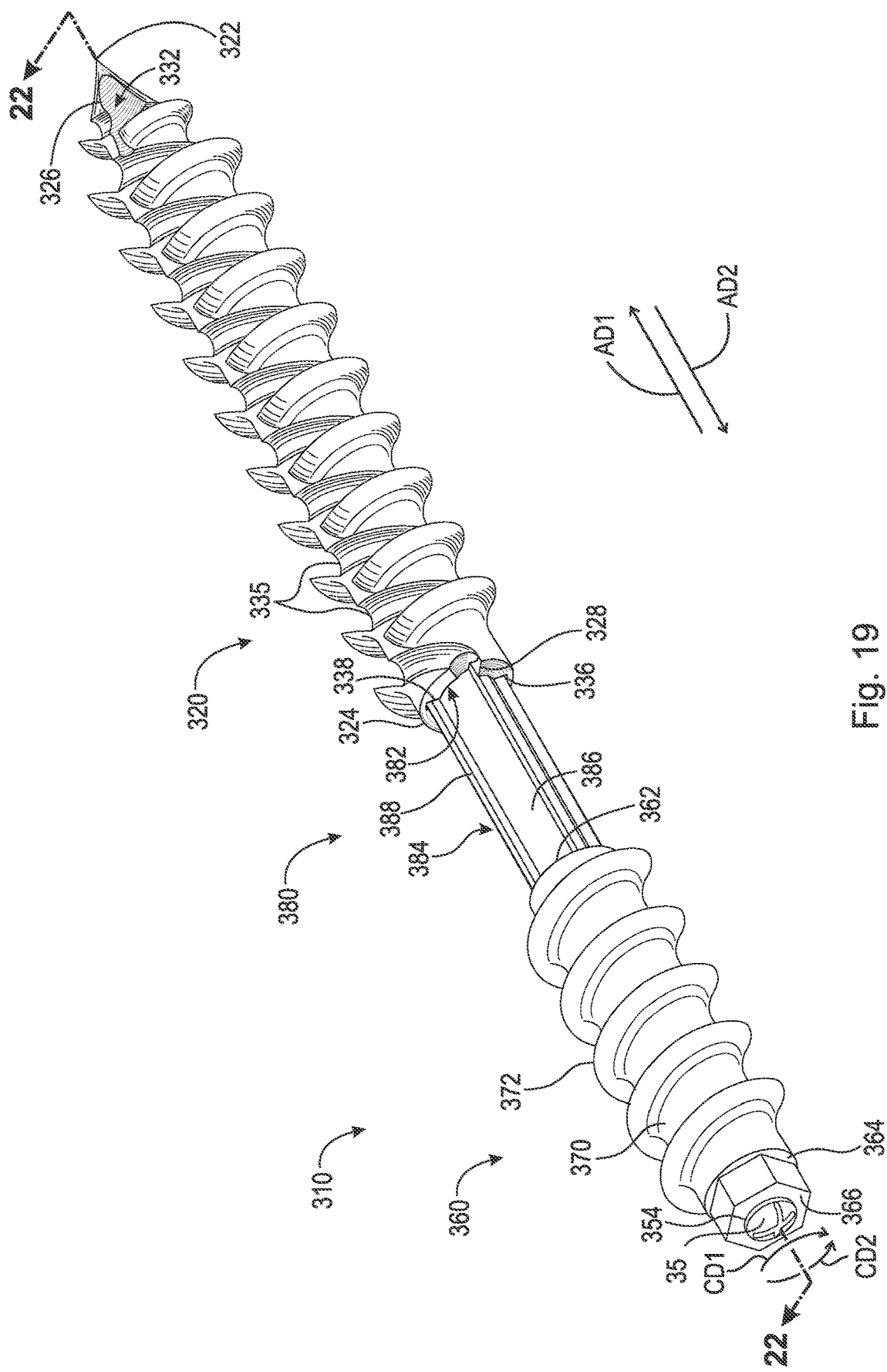
FIG. 19 is a rear perspective view of a fusion device assembly in a fully expanded state.
Figure 20:
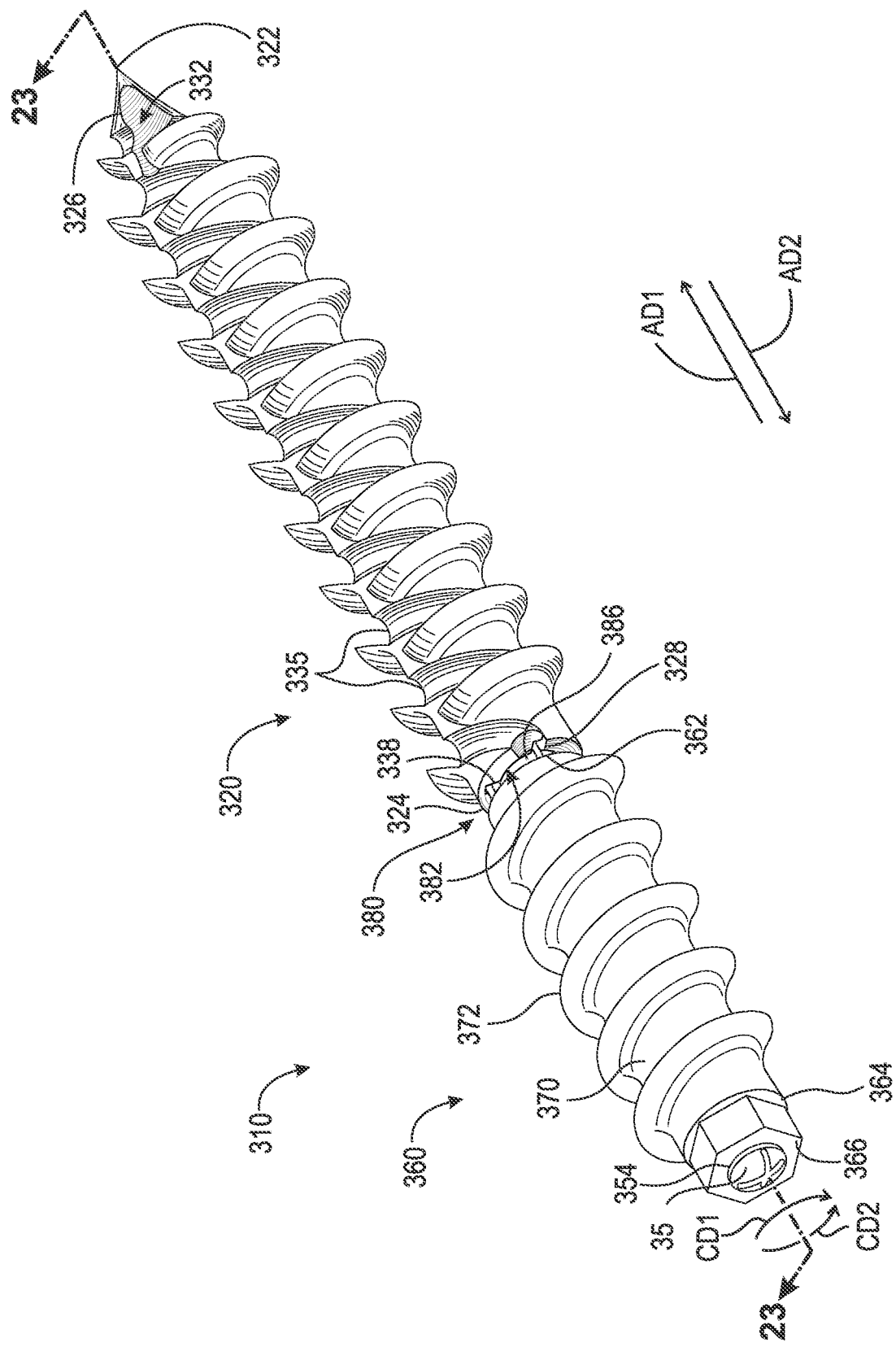
FIG. 20 is a rear perspective view of the fusion device assembly shown in FIG. 19, in a collapsed state.
Figure 21:
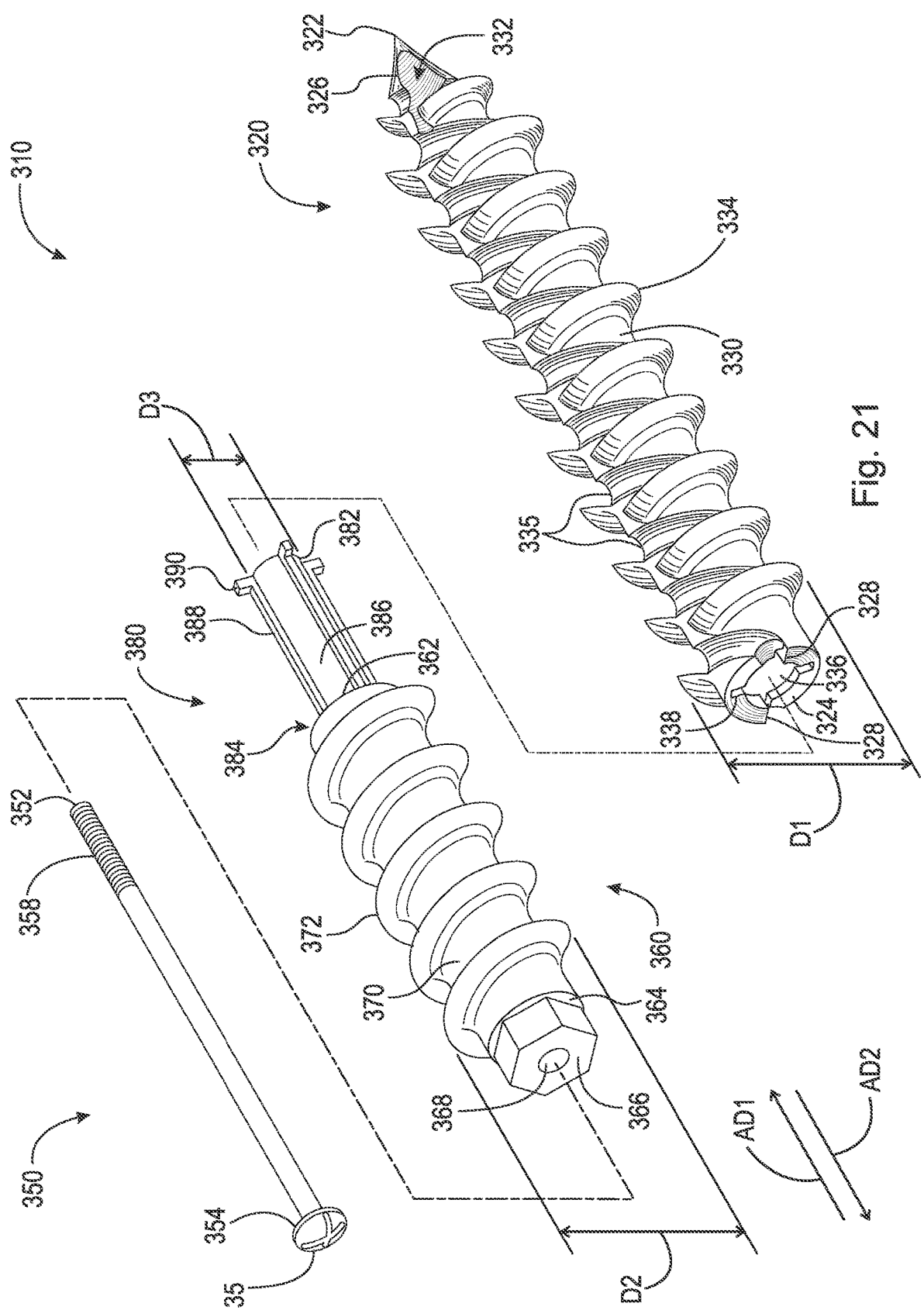
FIG. 21 is an exploded perspective view of the fusion device assembly shown in FIG. 19.
Figure 22:
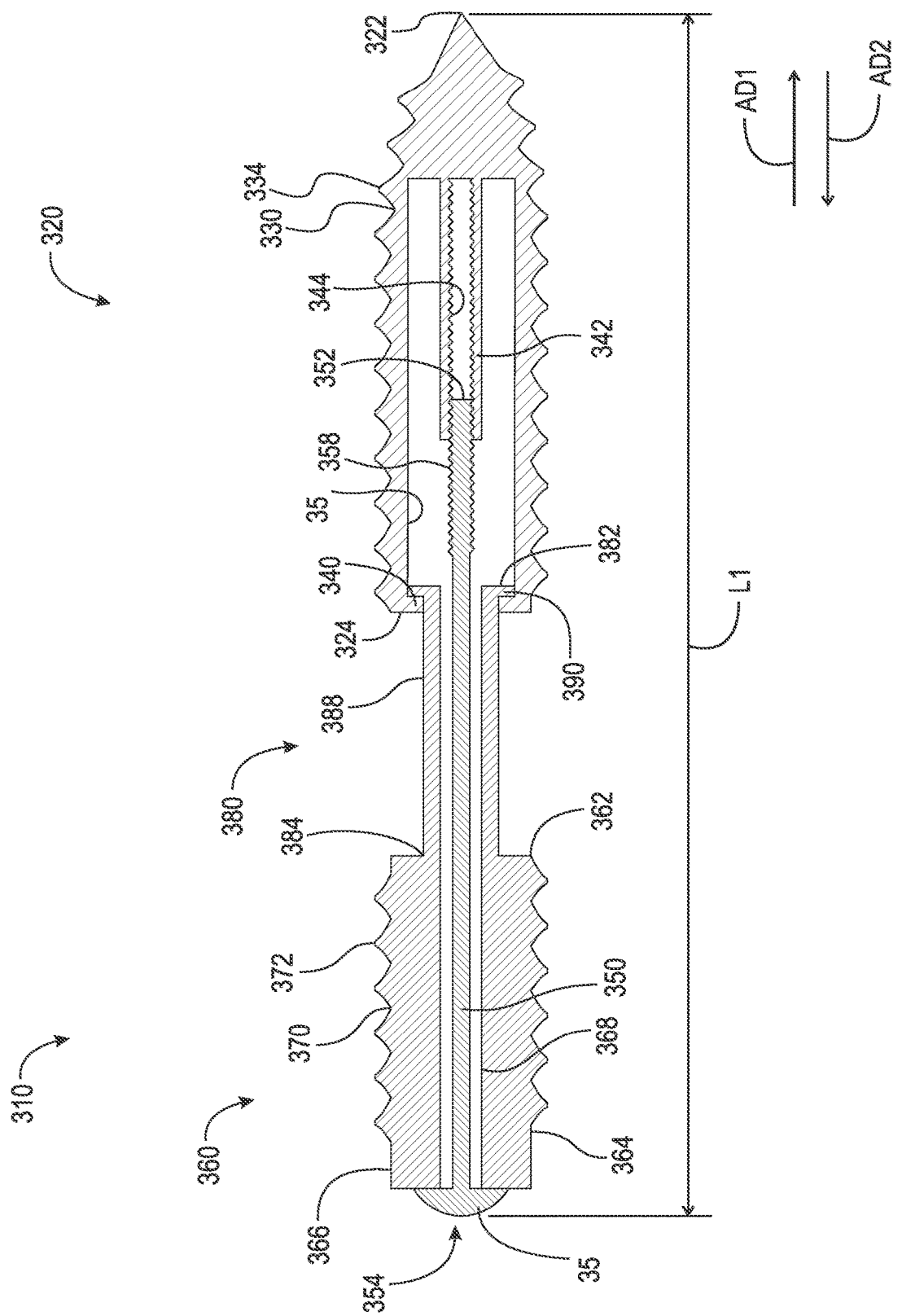
FIG. 22 is a cross-sectional view of the fusion device assembly taken generally along line 22-22 in FIG. 19.
Figure 23:
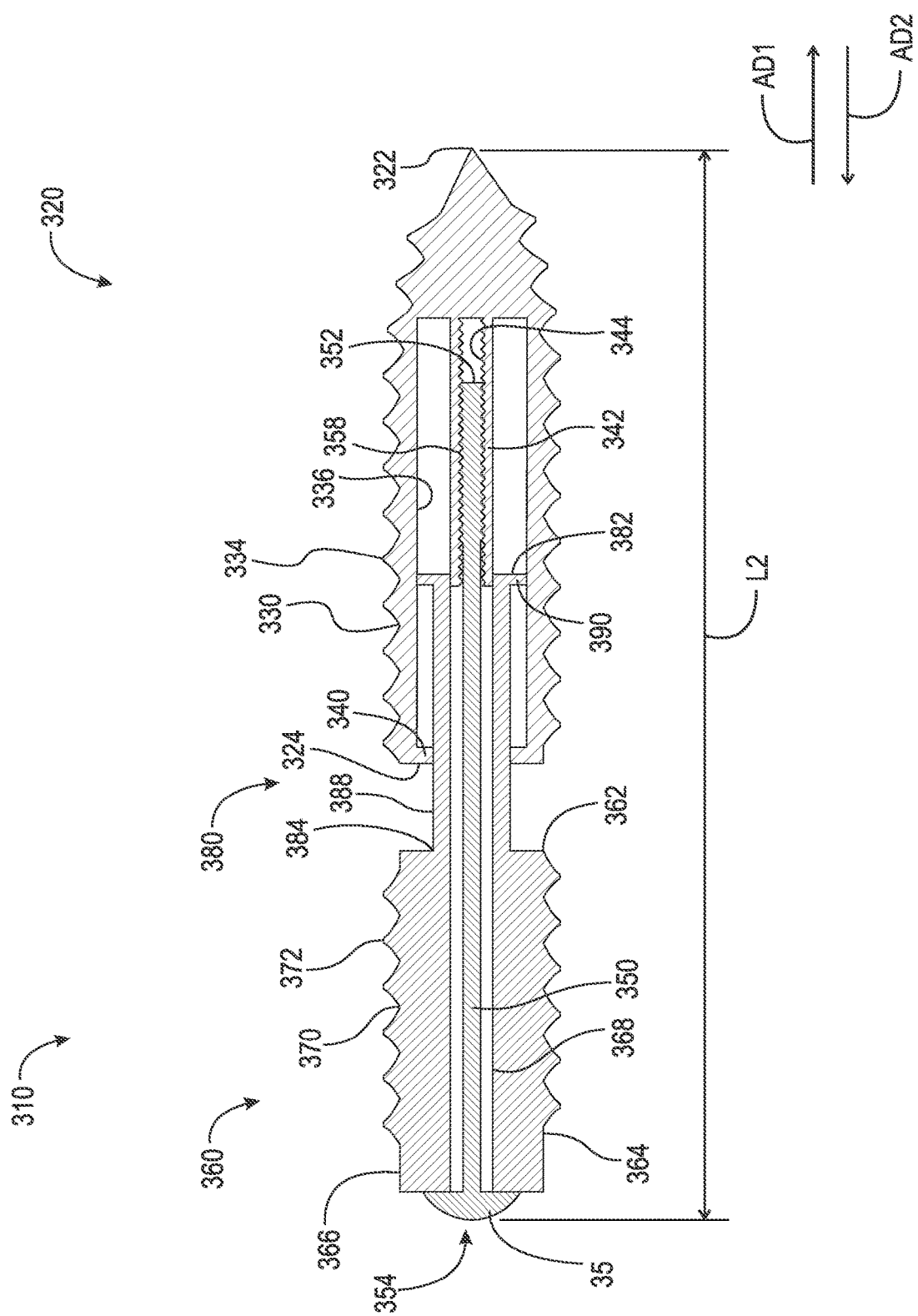
FIG. 23 is a cross-sectional view of the fusion device assembly taken generally along line 23-23 in FIG. 20.

FIG. 19 is a rear perspective view of fusion device assembly 310 in a fully expanded state. FIG. 20 is a rear perspective view of fusion device assembly 310 in a collapsed state. FIG. 21 is an exploded perspective view of fusion device assembly 310. FIG. 22 is a cross-sectional view of fusion device assembly 310 taken generally along line 22-22 in FIG. 19. FIG. 23 is a cross-sectional view of fusion device assembly taken generally along line 23-23 in FIG. 20. Fusion device assembly 310 generally comprises distal screw portion 320, proximal screw portion 360, bone graft section 380, and rod 350.

Screw portion 320 is generally cylindrical and comprises end 322, end 324, radially outward facing surface 330, and hole 336. Hole 336 is arranged in end 324 and extends in axial direction AD1 toward end 322. In some embodiments, and as shown, hole 336 comprises one or more notches for non-rotatable connection with bone graft section 380, as will be described in greater detail below. Radially outward facing surface 330 comprises threading 334 operatively arranged to secure fusion device assembly 310 to/within bone. Radially outward facing surface 330 further comprises one or more flutes, for example, flutes 332 and 335, and one or more cutting edges or blade tips, for example, cutting edges 326 and 328. Flute 332 extends from end 322 to end 324 and is operatively arranged to displace bone material (i.e., bone shavings) from end 322 to bone graft section 380. Cutting edge 326 is arranged on or adjacent to flute 332 at end 322. As fusion device assembly 310, specifically screw portion 320, is rotated in first circumferential direction CD1, cutting edge 326 cuts through bone producing bone shavings that are drawn back to bone graft section 380 via flute 332. Flute or reverse flute 335 extends from end 324 to end 322 and is operatively arranged to displace bone material (i.e., bone shavings) from bone graft section 380 to end 322. Cutting edge 328 is arranged on or adjacent to flute 335 at end 324. As fusion device assembly 310, specifically screw portion 320, is rotated in second circumferential direction CD2, cutting edge 328 cuts through bone arranged in bone graft section 380 (i.e., that has fused) producing bone shavings that are drawn toward end 322 via flute 335. As screw portion 320 comprises cutting edges on both ends, it can be said that screw portion 320 is a self-tapping screw in both axial directions.

As best shown in FIGS. 22-23, distal screw portion 320 further comprises tube 342 fixedly secured within hole 336. Tube 342 comprises radially inward facing surface 344 operatively arranged to engage with rod 350. In some embodiments, radially inward facing surface 344 comprises threading, which is threadably engageable with threading 358 of rod 350. In some embodiments, screw portion 320 does not comprise tube 344, but rather is solid and comprises a threaded hole arranged in hole 336 into which threading 358 engages. In some embodiments, end 324 further comprises radially inward extending flange 340.

Screw portion 360 is generally cylindrical and comprises end 362, end 364, radially outward facing surface 370, head 368, and hole 368. Head 368 is fixedly secured to end 364 and is operatively arranged to engage a tool such that fusion device assembly 310 can be rotated. In some embodiments, head 368 is hexagonal. It should be appreciated that head 368 may be any geometric shape suitable for engaging with a tool for rotation, for example, square, rectangular, octagonal, triangular, etc. Radially outward facing surface 370 comprises threading 372 operatively arranged to secure fusion device assembly 310 to/within bone.

Section 380 comprises end 382, end 384, and radially outward facing surface. It should be appreciated that radially outward facing surface 386 comprises a diameter that is less than the diameter of screw portion 320 and screw portion 360. For example, screw portion 320 comprises diameter D1, screw portion 360 comprises diameter D2, and section 380 comprises diameter D3. Diameter D3 is less than diameters D1 and D2. In some embodiments, diameter D1 is equal to diameter D2. Section 380 is operatively arranged to collect bone material or bone shavings created by cutting edge 326 for bone fusion across a joint or fracture, as will be described in greater detail below. End 384 is non-rotatably connected to end 362. In some embodiments, section 380 and screw portion 360 are integrally formed. End 382 is slidably engaged with hole 336. In some embodiments, radially outward facing surface 386 comprises one or more protrusions 388 operatively arranged to engage one or more notches 338 to non-rotatably connect section 380 and screw portion 320. In some embodiments, end 382 further comprises radially outward extending flange 390. Flange 390 is operatively arranged to engage flange 340 to prevent end 382 from being removed from hole 336. In some embodiments, hole 368 extends completely through screw portion 360 and section 380. Since section 380 is slidably engaged with screw portion 320, both section 380 and screw portion 360 are axially displaceable with respect to screw portion 320. However, it should be appreciated that screw portion 320, screw portion 360, and section 380 are all non-rotatably connection (i.e., rotationally locked).

Rod 350 is generally cylindrical and comprises end 352, end 356, and head 356. Head 356 is arranged at end 354 and is operatively arranged to engage end 364, specifically head 366. Rod 350 further comprises threading 358 arranged proximate end 352. End 352 is arranged to be fed through hole 368 and threading 358 is arranged to threadably engage with threaded hole or radially inward facing surface 344. Rod 350 is arranged radially inside of screw portion 360, section 380, and screw portion 320 which allows the overall length of fusion device assembly 310 to be shortened internally (i.e., an internal threaded rod). As rod 350, namely head 356, is rotated in circumferential direction CD1, screw portion 360 and section 380 are displaced in axial direction AD1 with respect to screw portion 320, thereby creating "compression" across the bone joint, as will be described in greater detail below. As head 356 is rotated in circumferential direction CD2, opposite circumferential direction CD1, section 380 and screw portion 360 are allowed to displace in axial direction AD2 with respect to screw portion 320. In some embodiments, as head 356 is rotated in circumferential direction CD2, section 380 and screw portion 360 are displaced in axial direction AD2 with respect to screw portion 320. As best shown in FIG. 22, when fusion device assembly 310 is in a fully expanded position, fusion device assembly 310 comprises overall length L1. As rod 350 is rotated in circumferential direction CD1, screw portion 360 and section 380 are displaced in axial direction AD1 with respect to screw portion 320, thereby decreasing the overall length of fusion device assembly 310, for example, to length L2 as shown in the collapsed position in FIG. 23.

Figure 24A:
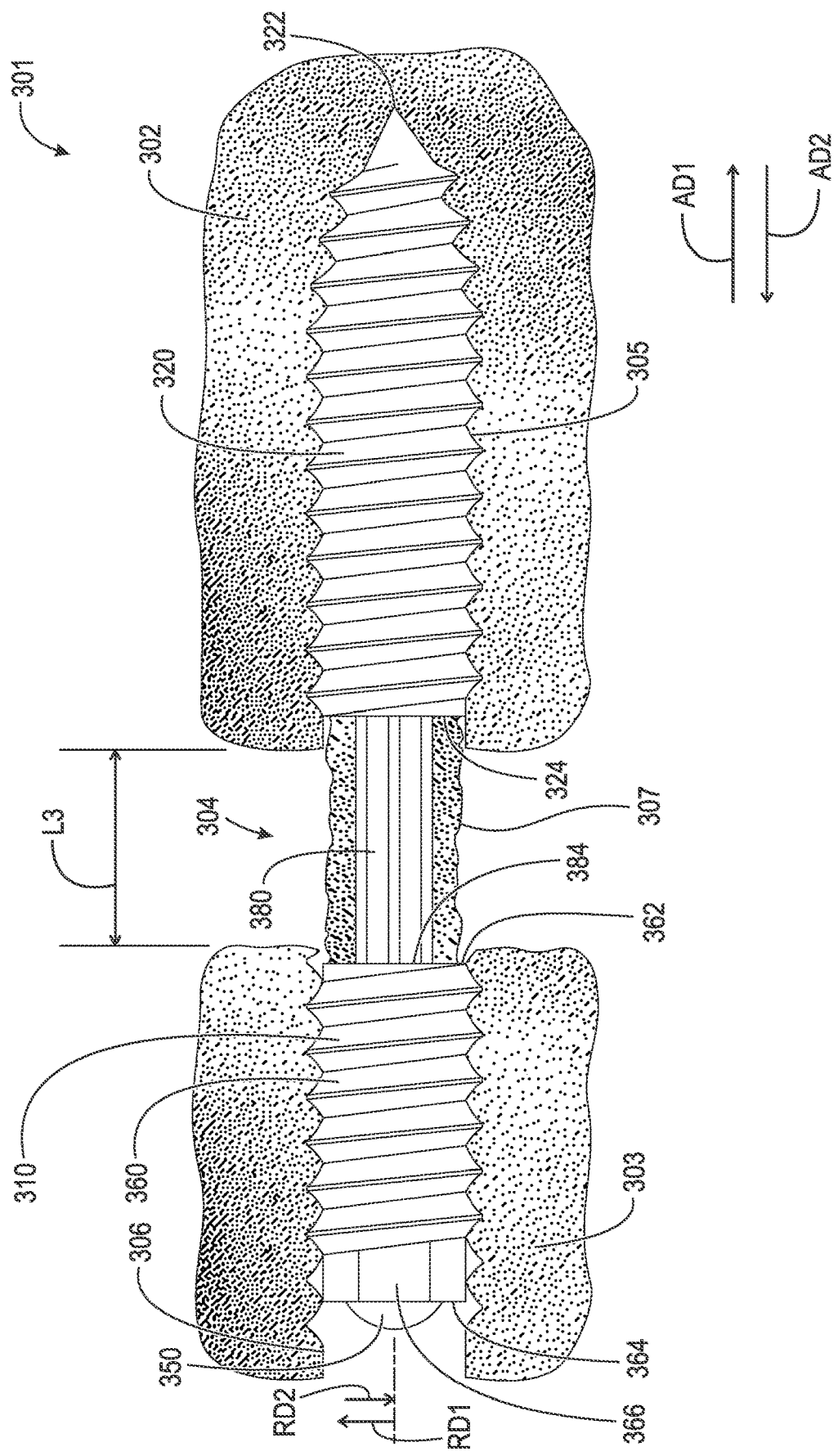
FIG. 24A is an elevational view of a fusion device assembly engaged with a bone structure in the fully expanded state.

FIG. 24A is an elevational view of fusion device assembly 310 engaged with bone structure 301 in the fully expanded state. Bone structure 301 represents a joint or a fracture and comprises at least two sections, for example, bony anatomy 302 and bony anatomy 303. Bony anatomies 302 and 303 are separated by space 304, which comprises length L3. Fusion device 310 is arranged to reduce the length of space 304. Fusion device assembly 310 is implanted first in bony anatomy 303 and then bony anatomy 302 by screwing it in, namely in circumferential direction CD1. As previously described, when rotating fusion device assembly 310 in circumferential direction CD1, cutting edge 326 bores a hole in the bony anatomy, for example, hole 305 in bony anatomy 302 and hole 306 in bony anatomy 303. Bone drillings or shavings 307 from the cutting of the bone are then fed back through flute 332 to section 380 where they are collected. When fusion device assembly 310 is fully implanted in bone structure 301, screw portion 320 should be at least partially engaged in bony anatomy 302, screw portion 360 should be at least partially engaged with bony anatomy 303, and section 380 should be at least partially aligned with space 304.

Figure 24B:
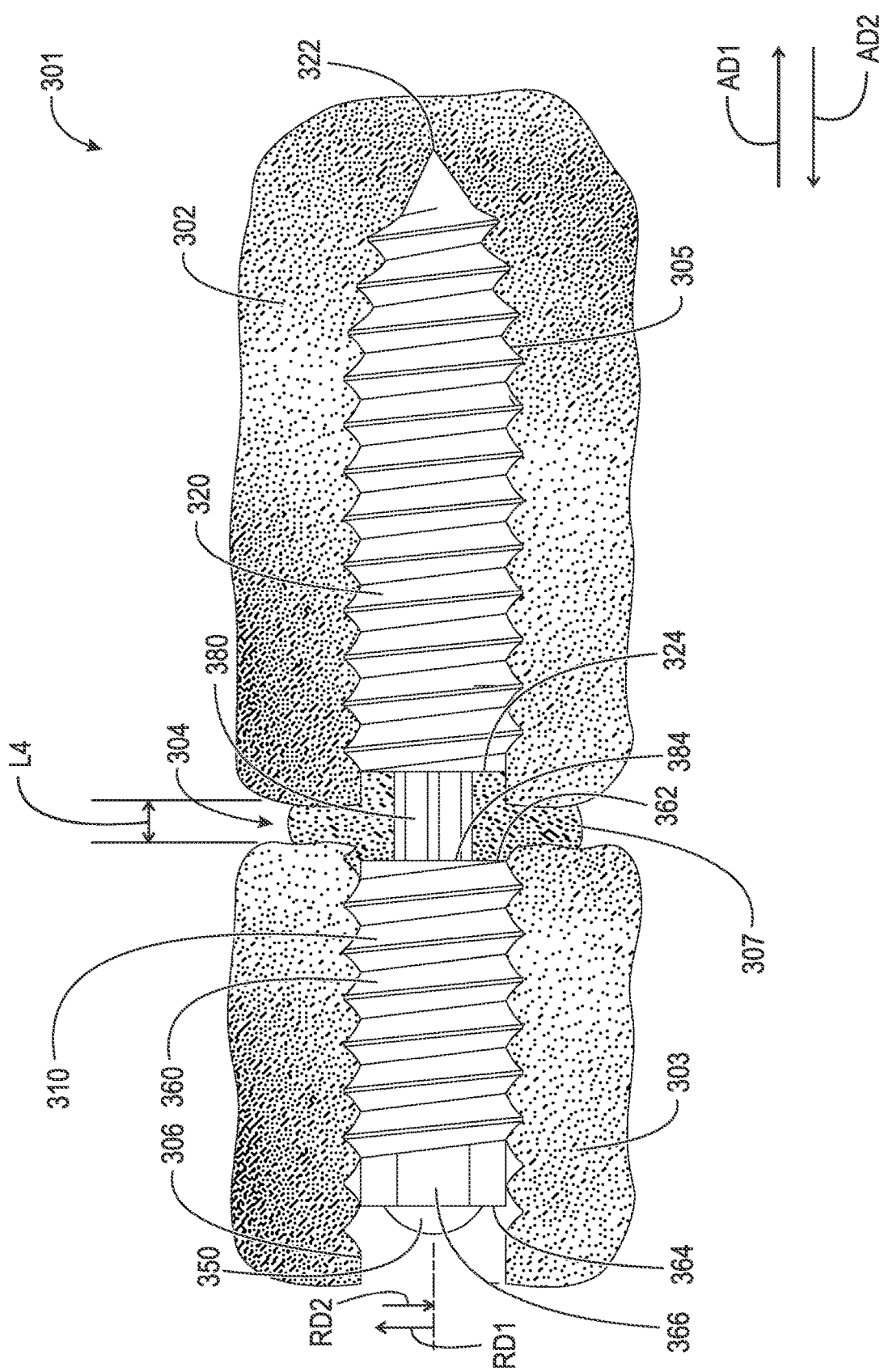
FIG. 24B is an elevational view of a fusion device assembly engaged with a bone structure in the collapsed state.

FIG. 24B is an elevational view of fusion device assembly 310 engaged with bone structure 301 in the collapsed state. Once fusion device assembly 310 is properly engaged with bone structure 301, as shown in FIG. 24B, head 366 is rotated in circumferential direction CD1 thereby displacing screw portion 360, section 380, and bony anatomy 303 in axial direction AD1 with respect to distal screw portion 320. Alternatively, as head 366 is rotated in circumferential direction CD1, screw portion 320 and bony anatomy 302 are displaced in axial direction AD2 with respect to screw portion 360, section 380, and bony anatomy 303. In both circumstances, the length of space 304 is reduced, for example to length L4, wherein bony anatomy 303 abuts or is arranged substantially proximate to bony anatomy 302. Additionally, as screw portions 320 and 360 are drawn together, ends 324 and 362 squeeze bone material or drillings 307 thereby forcing bone material 307 into contact with bony anatomies 302 and 303. The contact of the harvested bone material 307 with bony anatomies 302 and 303 completely surrounding section 380 provides for excellent bone fusion. Fusion device assembly 310 can be left in situ. Alternatively, after fusion occurs (i.e., bone material 307 has fused with bony anatomies 302 and 303 and is hardened), fusion device assembly 310 can be removed by rotating head 366 in circumferential direction CD2. As fusion device assembly 310 is rotated in circumferential direction CD2, cutting edge 328 cuts through newly fused bone and the drillings are fed through flute 335 toward end 322 allowing fusion device assembly 310 to be removed from bone structure 301. Furthermore, since cutting edge 328 will "re-bore" a hole to allow the removal of fusion device assembly 310, any lateral fusion between bony anatomies 302 and 303 will remain. This is advantageous because it allows the option of removing fusion device assembly 310 after fusion occurs, without affecting overall fusion of bone structure 301.

It will be appreciated that various aspects of the disclosure above and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

REFERENCE NUMERALS

2 Spinal column
4 Sacrum
6 Ilium
8 Sacroiliac joint
10 Fusion device assembly
12 Tool
20 Shaft
21 Through-bore
22 Section
24 End
26 End
28A Coupling lobe
28B Coupling lobe
28C Coupling lobe
30 Section
32 End
34 End
36 Section
38 End
40 End
50 Fusion device
51 Bore 52 End
53 Cutting edge/blade/tip/drill bit
54 End
56A Coupling lobe
56B Coupling lobe
56C Coupling lobe
58 Radially outward facing surface
60 Threading
62 Aperture(s)
64 Flute(s)
66 Aperture(s)
150 Fusion device
151 Bore
152 End
153 Cutting edge/blade/tip/drill bit
154 End
156A Coupling lobe
156B Coupling lobe
156C Coupling lobe
158 Radially outward facing surface
160 Threading
162 Aperture(s)
164 Flute(s)
166 Aperture(s)
168 Opening(s)
170 Radially inward facing surface
180 Expandable member(s)
182 Fixed pivot
184 Sliding pivot
186 Radially expanding pivot
190 Nut
191 Through-bore
192 Plate
194 Plate
196 Connector(s)
198 Connector(s)
250 Fusion device
251 Bore
252 End
253 Cutting edge/blade/tip/drill bit
254 End
256A Coupling lobe (not shown)
256B Coupling lobe (not shown)
256C Coupling lobe (not shown)
258 Radially outward facing surface
260 Threading
262 Aperture(s)
264 Flute(s)
266 Aperture(s)
268 Opening(s)
270 Radially inward facing surface
280 Expandable member(s)
290 Nut
291 Through-bore
292 Nut or plate
294 Connector(s)
301 Bone structure or joint
302 Bony anatomy
303 Bony anatomy
304 Space
305 Hole
306 Hole
307 Bone material or drillings
310 Fusion device assembly
320 Distal screw portion
322 End
324 End
326 Cutting edge or blade tip
328 Cutting edge or blade tip
330 Radially outward facing surface
332 Flute or flutes
334 Threading
335 Flute or flutes
336 Hole
338 Notch or notches
340 Flange
342 Tube
344 Radially inward facing surface
350 Rod
352 End
354 End
356 Head
358 Threading
360 Proximal screw portion
362 End
364 End
366 Head
368 Hole
370 Radially outward facing surface
372 Threading
380 Bone graft section
382 End
384 End
386 Radially outward facing surface
388 Protrusion or protrusions
390 Flange
AD1 Axial direction
AD2 Axial direction
CD1 Circumferential direction
CD2 Circumferential direction
D1 Diameter
D2 Diameter
D3 Diameter
L1 Length
L2 Length
L3 Length
L4 Length
RD1 Radial direction
RD2 Radial direction

What is claimed is:

1. A fusion device assembly for fusion of a joint, comprising:
a first screw portion, including:
a first distal end;
a first proximal end;
a first radially outward facing surface comprising a first diameter; and
a first hole;
a second screw portion, including:
a second distal end;
a second proximal end;
a head non-rotatably connected to the second proximal end;
a second radially outward facing surface comprising a second diameter; and
a second hole; and
a section, including:
a first end connected to the first proximal end;
a second end connected to the second distal end;
a third radially outward facing surface comprising a third diameter, the third diameter being less than the first diameter and the second diameter; and
a third hole, wherein the first hole, the second hole, and the third hole are in fluid communication.

2. The fusion device assembly as recited in claim 1, wherein the first screw portion further comprises:
  threading arranged on the first radially outward facing surface;
  at least one flute extending from the first distal end to the first proximal end; and
  at least one cutting edge operatively arranged to cut through bone.

3. The fusion device assembly as recited in claim 2, wherein the second screw portion further comprises threading arranged on the second radially outward facing surface.

4. The fusion device assembly as recited in claim 3, wherein the threading on the first radially outward facing surface includes a first pitch and the threading on the second radially outward facing surface includes a second pitch, the second pitch being different than the first pitch.

5. The fusion device as recited in claim 4, wherein the first pitch is greater than the second pitch.

6. The fusion device as recited in claim 4, wherein the first pitch is less than the second pitch.

7. The fusion device assembly as recited in claim 1, wherein the first screw portion comprises:
  a first flute including a first cutting edge, the first cutting edge arranged proximate the first distal end and arranged to cut when the first screw portion is displaced in a first circumferential direction; and
  a second flute including a second cutting edge, the second cutting edge arranged proximate the first proximal end and arranged to cut when the first screw portion is displaced in a second circumferential direction, opposite the first circumferential direction.

8. The fusion device assembly as recited in claim 1, wherein:
  the second hole is a through-hole extending from the second proximal end to the second distal end; and
  the third hole is a through-hole extending from the first end to the second end.

9. The fusion device assembly as recited in claim 1, wherein the first distal end comprises at least one cutting surface operatively arranged to cut through cortical bone.

10. The fusion device assembly as recited in claim 1, wherein the first distal end comprises a tapered diameter portion.

11. The fusion device assembly as recited in claim 1, further comprising an aperture extending radially through at least one of the first screw portion, the second screw portion, and the section.

12. The fusion device assembly as recited in claim 1, wherein the section does not comprise threading.

13. A fusion device assembly for fusion of a joint, comprising:
  a first screw portion, including:
    a first distal end comprising a tapered diameter portion;
    a first proximal end;
    a first radially outward facing surface comprising first threading and a first diameter; and
    a first hole;
  a second screw portion, including:
    a second distal end;
    a second proximal end;
    a second radially outward facing surface comprising second threading and a second diameter; and
    a second hole; and
  a section, including:
    a first end connected to the first proximal end;
    a second end connected to the second distal end;
    a third radially outward facing surface comprising a third diameter, the third diameter being less than the first diameter and the second diameter; and
    a third hole, wherein the first hole, the second hole, and the third hole are in fluid communication.

14. The fusion device assembly as recited in claim 13, wherein the first screw portion further comprises:
  at least one flute extending from the first distal end to the first proximal end; and
  at least one cutting edge operatively arranged to cut through bone.

15. The fusion device assembly as recited in claim 13, wherein the first threading includes a first pitch and the second threading includes a second pitch, the second pitch being different than the first pitch.

16. The fusion device as recited in claim 15, wherein the first pitch is greater than the second pitch.

17. The fusion device as recited in claim 15, wherein the first pitch is less than the second pitch.

18. The fusion device assembly as recited in claim 13, wherein the first screw portion comprises:
  a first flute including a first cutting edge, the first cutting edge arranged proximate the first distal end and arranged to cut when the first screw portion is displaced in a first circumferential direction; and
  a second flute including a second cutting edge, the second cutting edge arranged proximate the first proximal end and arranged to cut when the first screw portion is displaced in a second circumferential direction, opposite the first circumferential direction.

19. The fusion device assembly as recited in claim 13, wherein:
  the second hole is a through-hole extending from the second proximal end to the second distal end; and
  the third hole is a through-hole extending from the first end to the second end.

20. A fusion device assembly for fusion of a joint, comprising:
  a first screw portion, including:
    a first distal end comprising at least one cutting surface operatively arranged to cut through cortical bone;
    a first proximal end;
    a first radially outward facing surface comprising a first diameter; and
    a first hole;
  a second screw portion, including:
    a second distal end;
    a second proximal end;
    a second radially outward facing surface comprising a second diameter; and
    a second hole; and
  a section, including:
    a first end connected to the first proximal end;
    a second end connected to the second distal end;
    a third radially outward facing surface comprising a third diameter, the third diameter being less than the first diameter and the second diameter; and
    a third hole, wherein the first hole, the second hole, and the third hole are in fluid communication.

* * * * *